US005202343A

United States Patent [19]

Coates et al.

[11] Patent Number: 5,202,343

[45] Date of Patent: Apr. 13, 1993

[54] TRICYCLIC KETONES USEFUL AS $HT_3$-RECEPTOR ANTAGONISTS

[75] Inventors: Ian H. Coates, Hertford; John Bradshaw; James A. Bell, both of Royston; David C. Humber, London; George B. Ewan, Gerrards Cross; William L. Mitchell, London; Barry J. Price, Tewin Wood, all of England

[73] Assignee: Glaxo Group Limited, London, England

[21] Appl. No.: 887,607

[22] Filed: May 22, 1992

Related U.S. Application Data

[60] Continuation of Ser. No. 770,720, Oct. 4, 1991, abandoned, which is a continuation of Ser. No. 476,537, Feb. 7, 1990, abandoned, which is a continuation of Ser. No. 320,622, Mar. 8, 1989, abandoned, which is a division of Ser. No. 281,031, Dec. 7, 1988, Pat. No. 4,859,662, which is a continuation of Ser. No. 199,792, May 27, 1988, abandoned, which is a continuation-in-part of Ser. No. 126,202, Nov. 27, 1987, Pat. No. 4,822,881.

[30] Foreign Application Priority Data

| | | | |
|---|---|---|---|
| Nov. 28, 1986 | [GB] | United Kingdom | 8628473 |
| Nov. 12, 1987 | [GB] | United Kingdom | 8726537 |
| May 20, 1989 | [GB] | United Kingdom | 8812002 |

[51] Int. Cl.[5] .................... A61K 31/415; C07D 403/06

[52] U.S. Cl. .................................. 514/397; 548/311.4

[58] Field of Search ......................... 548/336; 514/397

[56] References Cited

U.S. PATENT DOCUMENTS

| | | | |
|---|---|---|---|
| 4,808,581 | 2/1989 | Oxford et al. | 514/212 |
| 4,814,344 | 3/1989 | Humber et al. | 514/397 |
| 4,822,881 | 4/1989 | Coates et al. | 540/603 |
| 4,859,662 | 8/1989 | Coates et al. | 514/212 |
| 4,950,681 | 8/1990 | Cavalla et al. | 548/336 |

FOREIGN PATENT DOCUMENTS 2153821 8/1985 United Kingdom .

*Primary Examiner*—Mary C. Lee
*Assistant Examiner*—Lenora Ava Miltenberger
*Attorney, Agent, or Firm*—Bacon & Thomas

[57] ABSTRACT

The invention relates to compounds of the general formula (I):

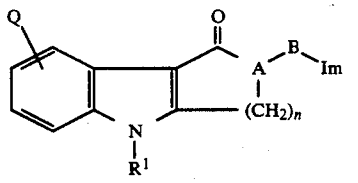

(I)

wherein Im represents an imidazolyl group of the formula:

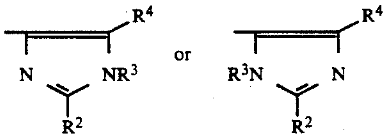

$R^1$ represents a hydrogen atom or a group selected from $C_{1-6}$alkyl, $C_{3-6}$alkenyl, $C_{3-10}$alkynyl, $C_{3-7}$cycloalkyl, $C_{3-7}$cycloalkyl$C_{1-4}$alkyl, phenyl, phenyl$C_{1-3}$alkyl, $-CO_2R^5$, $-COR^5$, $-CONR^5R^6$ or $-SO_2R^5$;

$R^5$ and $R^6$, which may be the same or different, each represents a hydrogen atom, a $C_{1-6}$alkyl or $C_{3-7}$cycloalkyl group, or a phenyl or phenyl$C_{1-4}$alkyl group, in which the phenyl group is optionally substituted by one or more $C_{1-4}$ alkyl, $C_{1-4}$alkoxy or hydroxy groups or halogen atoms, with the proviso that $R^5$ does not represent a hydrogen atom when $R^1$ represents a group $-CO_2R^5$ or $-SO_2R^5$;

one of the groups represented by $R^2$, $R^3$ and $R^4$ is a hydrogen atom or a $C_{1-6}$alkyl, $C_{3-7}$cycloalkyl, $C_{3-6}$alkenyl, phenyl or phenyl$C_{1-3}$alkyl group, and each of the other two groups, which may be the same or different, represents a hydrogen atom or a $C_{1-6}$alkyl group;

Q represents a hydrogen or a halogen atom, or a hy- (Abstract continued on next page.)

droxy, $C_{1-4}$alkoxy, phenyl$C_{1-3}$ alkoxy or $C_{1-6}$alkyl group or a group $—NR^7R^8$ or $—CONR^7R^8$;

$R^7$ and $R^8$, which may be the same or different, each represents a hydrogen atom or a $C_{1-4}$alkyl or $C_{3-4}$alkenyl group, or together with the nitrogen atom to which they are attached form a saturated 5 to 7 membered ring;

n represents 1, 2 or 3; and

A-B represents the group $CH—CH_2$ or $C{=}CH$; and physiologically acceptable salts and solvates thereof.

The compounds are potent and selective antagonists of the effect of 5-HT at 5-$HT_3$ receptors and are useful, for example, in the treatment of psychotic disorders, anxiety, and nausea and vomiting.

5 Claims, No Drawings

TRICYCLIC KETONES USEFUL AS $HT_3$-RECEPTOR ANTAGONISTS

This application is a continuation of application Ser. No. 07/770,720, filed Oct. 4, 1991, now abandoned, which is a continuation of application Ser. No. 07/476,537, filed Feb. 7, 1990, now abandoned, which is a divisional of application Ser. No. 07/281,031, filed Dec. 7, 1988, now U.S. Pat. No. 4,859,662, which is a continuation of application Ser. No. 07/199,792, filed May 27, 1988, now abandoned, which is a continuation-in-part of applicaiton Ser. No. 07,126,202, filed Nov. 27, 1987, which is now U.S. Pat. No. 4,822,881.

This invention relates to tricyclic ketones, to processes for their preparation, to pharmaceutical compositions containing them and to their medical use. In particular the invention relates to compounds which act upon 5-hydroxytryptamine (5-HT) receptors of the type located on terminals of primary afferent nerves.

Compounds having antagonist activity at 'neuronal' 5-HT receptors of the type located on primary afferent nerves have been described previously.

Thus for example published UK Patent Specification No. 2153821A and published European Patent Specification No. 191562 disclose tetrahydrocarbazolones of the general formula

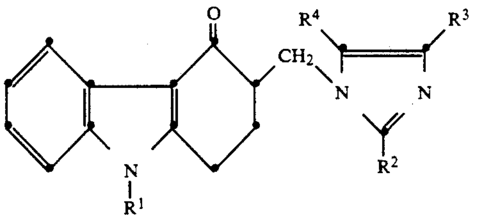

wherein $R^1$ represents a hydrogen atom or a $C_{1-10}$alkyl, $C_{3-7}$cycloalkyl, $C_{3-7}$cycloalkyl$C_{1-4}$alkyl, $C_{3-6}$alkenyl, $C_{3-10}$alkynyl, phenyl or phenyl$C_{1-3}$alkyl group, and one of the groups represented by $R^2$, $R^3$ and $R^4$ is a hydrogen atom or a $C_{1-6}$alkyl, $C_{3-7}$cycloalkyl, $C_{2-6}$alkenyl or phenyl$C_{1-3}$alkyl group and each of the other two groups, which may be the same or different, represents a hydrogen atom or a $C_{1-6}$ alkyl group.

We have now found a novel group of compounds which differ in structure from those described previously, and which are potent antagonists of the effect of 5-HT at 5-HT 'neuronal' receptors.

Thus, in one aspect the present invention provides a tricyclic ketone of the general formula (I):

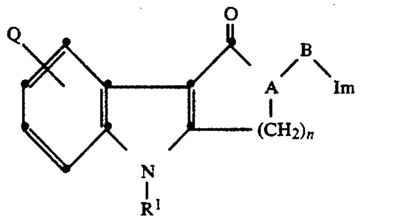

(I)

wherein Im represents an imidazolyl group of the formula:

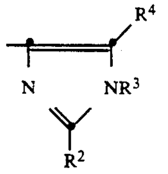

or

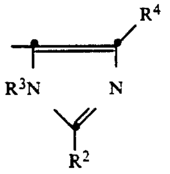

$R^1$ represents a hydrogen atom or a group selected from $C_{1-6}$alkyl, $C_{3-6}$ alkyenyl, $C_{3-10}$ alkynyl, $C_{3-7}$ cycloalkyl, $C_{3-7}$cycloalkyl$C_{1-4}$alkyl, phenyl, phenyl$C_{1-3}$alkyl, $-CO_2R^5$, $-COR^5$, $-CONR^5R^6$ or $-SO_2R^5$ (wherein $R^5$ and $R^6$, which may be the same or different, each represents a hydrogen atom, a $C_{1-6}$ alkyl or $C_{3-7}$ cycloalkyl group, or a phenyl or phenyl$C_{1-4}$alkyl group, in which the phenyl group is optionally substituted by one or more $C_{1-4}$ alkyl, $C_{1-4}$ alkoxy or hydroxy groups or halogen atoms, with the proviso that $R^5$ does not represent a hydrogen atom when $R^1$ represents a group $-CO_2R^5$ or $-SO_2R^5$); one of the groups represented by $R^2R^3$ and $R^4$ is a hydrogen atom or a $C_{1-6}$ alkyl, $C_{3-7}$ cycloalkyl, $C_{3-6}$ alkenyl, phenyl or phenyl$C_{1-3}$alkyl group, and each of the other two groups, which may be the same or different, represents a hydrogen atom or a $C_{1-6}$ alkyl group; Q represents a hydrogen or a halogen atom, or a hydroxyl, $C_{1-4}$ alkoxy, phenyl$C_{1-3}$alkoxy or $C_{1-6}$ alkyl group or a group $-NR^7R^8$ or $-CONR^7R^8$ wherein $R^7$ and $R^8$, which may be the same or different, each represents a hydrogen atom or a $C_{1-4}$ alkyl or $C_{3-4}$ alkenyl group, or together with the nitrogen atom to which they are attached form a saturated 5 to 7 membered ring);

n represents 1, 2 or 3;

and A-B represents the group $CH-CH_2$ or $C=CH$; and physiologically acceptable salts and solvates thereof.

Suitable physiologically acceptable salts of the compounds of general formula (I) include acid addition salts formed with organic or inorganic acids for example, hydrochlorides, hydrobromides, sulphates, alkyl- or arylsulphonates (e.g. methanesulphonates or p-toluenesulphoates), phosphates, acetates, citrates, succinates, tartrates, fumarates and maleates. The solvates may, for example, be hydrates.

It will be appreciated that when A-B represents $CH-CH_2$ the carbon atom A is asymmetric and may exist in the R- or S- configuration. Furthermore, depending on the nature of the substituents A-B, $R^1$, $R^2$, $R^3$, $R^4$ and Q, centres of optical and geometric isomerism may occur elsewhere in the molecule. All optical isomers of compounds of general formula (I) and their mixtures including the racemic mixtures thereof, and all the geometric isomers of compounds of formula (I), are embraced by the invention.

Referring to the general formula (I), and alkyl groups represented by $R^1$, $R^2$, $R^3$, $R^4$, $R^5$, $R^6$, $R^7$, $R^8$ and Q may be straight chain or branched chain alkyl groups, for example, methyl, ethyl, propyl, prop-2-yl, butyl, but-2-yl or 2-methylprop-2-yl, and, in the case of $R^1$-$R^6$ and Q, pentyl, pent-3-yl or hexyl. An alkenyl group may be, for example, a propenyl or butenyl group. An alkynyl group may be, for example, a prop-2-ynyl or oct-2-ynyl group.

It is understood that when $R^1$ or $R^3$ represents a $C_{3-6}$alkenyl group or $R^1$ represents a $C_{3-10}$ alkynyl group, or $R^7$ or $R^8$ represents a $C_{3-4}$ alkenyl group, the double or triple bond may not be adjacent to the nitrogen atom.

A phenyl$C_{1-3}$ alkyl group (as such or as part of a phenyl$C_{1-3}$alkoxyl group) may be, for example, a benzyl, phenethyl or 3-phenylpropyl group. A cycloalkyl group (as such or as part of a cycloalkylalkyl group) may be, for example, a cyclopropyl, cyclobutyl, cyclopentyl, cyclohexyl or cycloheptyl group. When $R^1$ represents a $C_{3-7}$ cycloalkyl $C_{1-4}$ alkyl group, the alkyl moiety may be, for example, a methyl, ethyl, propyl, prop-2-yl or butyl group. When Q represents a $C_{1-4}$ alkoxyl group it may be, for example, a methoxy group. When Q represents a halogen atom it may be, for example, a fluorine, chlorine or bromine atom. The substituent Q may be at the a, b, c or d position of the indole moiety:

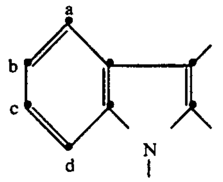

A preferred class of compounds of formula (I) is that wherein $R^1$ represents a hydrogen atom or a $C_{1-3}$ alkyl (e.g. methyl), $C_{3-4}$ alkenyl (e.g. prop-2-enyl), $C_{3-4}$ alkynyl (e.g. prop-2-ynyl), $C_{5-6}$cycloalkyl (e.g. cyclopentyl), $C_{5-6}$cycloalkylemthyl (e.g. cyclopentylmethyl), phenyl$C_{1-2}$alkyl (e.g. benzyl), $C_{1-3}$ alkoxycarbonyl (e.g. methoxycarbonyl), N,N-di$C_{1-3}$alkylcarboxamido (e.g. N,N-dimethylcarboxamide) or phenylsulphonyl group. More preferably $R^1$ represents a hydrogen atom or a $C_{1-3}$ alkyl (e.g. methyl), $C_{3-4}$ alkenyl (e.g. prop-2-enyl), $C_{3-4}$ alkynyl (e.g. prop-2-ynyl), $C_{5-6}$cycloalkylmethyl (e.g. cyclopentylmethyl), phenyl $C_{1-2}$ alkyl (e.g. benzyl), $C_{1-3}$ alkoxycarbonyl (e.g. methoxycarbonyl), or N,N-di$C_{1-3}$alkylcarboxamido (e.g. N,N-dimethylcarboxamido) group. Most preferably $R^1$ represents a hydrogen atom or a $C_{1-3}$ alkyl (e.g. methyl), $C_{3-4}$ alkenyl (e.g. prop-2-enyl), $C_{3-4}$alkynyl (e.g. prop-2-ynyl), $C_{5-6}$ cycloalkylemthyl (e.g. cyclopentylmethyl), phenyl$C_{1-2}$ alkyl (e.g. benzyl) or N,N-di$C_{1-3}$alkylcarboxamido (e.g. N,N-dimethylcarboxamido) group.

Another preferred class of compounds of formula (I) is that wherein $R^2$ represents a hydrogen atom or a $C_{1-3}$ alkyl (e.g. methyl) group, more preferably a hydrogen atom.

Another preferred class of compounds of formula (I) is that wherein $R^3$ represents a hydrogen atom or a $C_{1-3}$ alkyl (e.g. methyl) group, more preferably a hydrogen atom.

A further preferred class of compounds of formula (I) is that wherein $R^4$ represents a hydrogen atom or a $C_{1-3}$ alkyl (e.g. methyl) group. Most preferably $R^4$ represents a methyl group.

Another preferred class of compounds of formula (I) is that wherein Q represents a hydrogen atom, a halogen (e.g. fluorine) atom or a hydroxy, a $C_{1-3}$ alkoxy (e.g. methoxy) or a $C_{1-3}$ alkyl, (e.g. methyl) group. More preferably Q represents a hydrogen atom, a halogen (e.g. fluorine) atom or a hydroxy group. Most preferably Q represents a hydrogen or a fluorine atom.

When Q represents a substituent other than a hydrogen atom, Q is preferably at the b- or c- position of the indole moiety. Another preferred class of compounds in which Q represents a substituent other than a hydrogen atom is that wherein Q is at the d- position of the indole moiety.

Another preferred class of compounds of formula (I) is that wherein A-B represent CH—$CH_2$.

A further preferred class of compounds of formula (I) is that wherein n represents 2 or 3, more particularly 2.

A preferred group of compounds of formula (I) is that wherein $R^1$ represents a hydrogen atom or a $C_{1-3}$ alkyl, $C_{3-4}$alkenyl, $C_{3-4}$alkynyl, $C_{5-6}$cycloalkylmethyl, phenyl $C_{1-2}$ alkyl, $C_{1-3}$alkoxycarbonyl or N,N-di$C_{1-3}$alkylcarboxamido group; $R^2$ and $R^3$ each represent a hydrogen atom; $R^4$ represents a hydrogen atom or a $C_{1-3}$ alkyl group; Q represents a hydrogen or a halogen atom or a hydroxyl group; A-B represents CH—$CH_2$ or C═CH; and n represents 2 or 3.

A particularly preferred group of compounds of formula (I) is that wherein $R^1$ represents a hydrogen atom or a methyl, prop-2-enyl, prop-2-ynyl, cyclopentylmethyl, benzyl or N,N-dimethylcarboxamido group; $R^2$ and $R^3$ each represent a hydrogen atom; $R^4$ represents a methyl group; Q represents a hydrogen or a fluorine atom; A-B represents CH—$CH_2$; and n represents 2 or 3.

Within the above preferred and particularly preferred groups of compounds an especially important group of compounds is that in which n represents 2.

Preferred compounds according to the invention are:
6-fluoro-1,2,3,9-tetrahydro-9-methyl-3-[(5-methyl-1H-imidazol-4-yl)methyl]-4H-carbazol-4-one;
1,2,3,9-tetrahydro-3-[(5-methyl-1H-imidazol-4-yl)methyl]-4H-carbazol-4-one;
9-(cyclopenylmethyl)-1,2,3,9-tetrahydro-3-[(5-methyl-1H-imidazol-4-yl) methyl]-4H-carbazol-4-one;
8-fluoro-1,2,3,9-tetrahydro-9-methyl-3-[(5-methyl-1H-imidazol-4-yl)methyl]-4H-carbazol-4-one; 8-fluoro-1,2,3,9-tetrahydro-3-[(5-methyl-1H-imidazol-4-yl)methyl]-4H-carbazol-4one;
1,2,3,9-tetrahydro-3-[(5-methyl-1H-imidazol-4-yl)methyl]-9-(2-propynyl)-4H-carbazol-4-one;
a further preferred compound according to the invention is 6,7,8, 9-tetrahydro-5-methyl-9-[(5-methyl-1H-imidazol-4-yl)methyl]-cyclohept[b]indol-10(5H)-one;
and their physiologically acceptable salts and solvates.

A particularly preferred compound according to the invention is 1,2,3,9-tetrahydro-9-methyl-3-[(5-methyl-1H-imidazol-4-yl)methyl]-4H-carbazol -4-one and its physiologically acceptable salts and solvates (e.g. hydrates).

Preferred forms of this compound are the hydrochloride and the maleate. A particularly preferred form is the hydrochloride monohydrate.

It will be appreciated that the invention extends to other physiologically acceptable equivalents of the compounds according to the invention, i.e. physiologically acceptable compounds which are converted in vivo into the parent compound of formula (I).

Compounds of the invention are potent and selective antagonists of 5-HT-induced responses of the rat isolated vagus nerve preparation and thus act as potent and selective antagonists of the 'neuronal' 5-HT receptor type located on primary afferent nerves. Receptors of this type are now designated as 5-$HT_3$ receptors. Such receptors are also present in the central nervous system. 5-HT occurs widely in the neuronal pathways in the central nervous system and disturbance of these 5-HT containing pathways is known to alter behavioural syndromes such as mood, psychomotor activity, appetite and memory.

Compounds of formula (I), which antagonise the effect of 5-HT at 5-$HT_3$ receptors, are useful in the treatment of conditions such as psychotic disorders (e.g. schizophrenia and mania); anxiety; and nausea and vomiting, particularly that associated with cancer chemotherapy and radiotherapy. Compounds of formula (I) are also useful in the treatment of gastric stasis; symptoms of gastrointestinal dysfunction such as occur with dyspepsia, peptic ulcer, reflux oesophagitis, flatulence and irritable bowel syndrome; migraine; and pain. Compounds of formula (I) may also be used in the treatment of dependency on drugs and substances of abuse, depression and dementia and other cognitive disorders.

Unlike existing drug treatments for certain of the above conditions, the compounds of the invention, because of their high selectivity for 5-$HT_3$ receptors, would not be expected to produce undesirable side effects. Thus, for example, neuroleptic drugs may exhibit extrapyramidal effects, such as tardive dyskinesia, and benzodiazepines may cause dependence.

According to another aspect, the invention provides a method of treatment of a human or animal subject suffering from a psychotic disorder such as schizophrenia or mania; or from anxiety; nausea or vomiting, particularly that associated with cancer chemotherapy and radiotherapy; gastric stasis; symptoms of gastrointestinal dysfunction such as dyspepsia, reflux oesophagitis, peptic ulcer, flatulence and irritable bowel syndrome; migraine; or pain, which comprises administering an effective amount of a compound of formula(I) or a physiologically acceptable salt or solvate thereof.

Accordingly, the invention also provides a pharmaceutical composition which comprises at least one compound selected from tricyclic ketones derivatives of the general formula(I), their physiologically acceptable salts and solvates (e.g. hydrates), for use in human or veterinary medicine, and formulated for administration by any convenient route.

Such compositions may be formulated in conventional manner using one or more physiologically acceptable carriers and/or excipients.

Thus the compounds according to the invention may be formulated for oral, buccal, parenteral, rectal or trasdermal administration or in a form suitable for administration by inhalation or insufflation (either through the mouth or the nose).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia);

non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds of the invention may be formulated for parenteral administration by injection e.g. by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds of the invention may also be formulated in rectal compositions such as suppositories or retention enemas, e.g. containing conventional suppository bases such as cocoa butter or other glycerides.

In addition to the formulations described previously, the compounds of the invention may also be formulated as depot preparations. Such long acting formulations may be administered by implantation (for example subcutaneously, transcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

For administration by inhalation the compounds according to the invention are conveniently delivered in the form of an aerosol spray presentation from pressurised packs or a nebuliser, with the use of a suitable propellant, e.g. dichlorodifluoromethane, trichlorofluoromethane, dichlorotetrafluoroethane, carbon dioxide or other suitable gas. In the case of a pressurised aerosol the dosage unit may be determined by providing a value to deliver a metered amount. Capsules and cartridges of e.g. gelatin for use in an inhaler or insufflator may be formulated containing a powder mix of a compound of the invention and a suitable powder base such as lactose or starch.

For intranasal administration, the compound according to the invention may be formulated as solutions for administration via a suitable metered or unit dose device or alternatively as a powder mix with a suitable carrier for administration using a suitable delivery device.

The compounds of formula (I) may also be administered in combination with other therapeutic agents. Thus, for example, in the treatment of gastric stasis, symptoms of gastrointestinal dysfunction and nausea and vomiting, the compounds of formula (I) may be administered in combination with antisecretory agents such as histamine $H_2$-receptor antagonists (e.g. ranitidine, sufotidine or 1-methyl-5-[[3-[3-(1-peperidinylmethyl)phenoxy]propyl]amino]-1H-1,2,4-triazole -3-methanol) or $H^+K^+$ATPase inhibitors (e.g. omeprazole).

A proposed dose of the compounds of the invention for administration to man (of approximately 70 kg body weight) is 0.001 to 100 mg, for example 0.01 to 50 mg, more preferably 0.1 to 20 mg of the active ingredient per unit dose which could be administered, for example, 1 to 4 times per day. The dose will depend on the route of administration and the condition being treated. It will be appreciated that it may be necessary to make routine variations to the dosage depending on the age and weight of the patient as well as the severity of the condition to be treated.

According to another aspect of the invention, compounds of general formula (I), and physiologically acceptable salts or solvates thereof, may be prepared by the general methods outlined hereinafter. In the following description, the groups $R^1$, $R^2$, $R^3$, $R^4$, A, B, Q, n and Im are as defined for compounds of general formula (I) unless otherwise stated.

According to a first general process (A), a compound of general formula (I) wherein A-B represents the group C═CH, may be prepared by dehydrating a compound of formula (II):

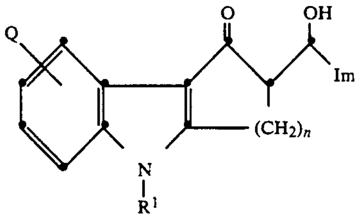

(II)

or a protected derivative thereof, followed where necessary by removal of any protecting groups.

The dehydration process may be affected using conventional methods, for example by using an organic or mineral acid (e.g. p-toluenesulphonic, methanesulphonic, trifluoroacetic or hydrochloric acid) in a suitable solvent such as an ether (e.g. tetrahydrofuran0, an alcohol (e.g. methanol), or glacial acetic acid, at a temperature in the range 0° to 100°.

According to a particular embodiment of this process, a compound of general formula (I), wherein A-B represents the group C═CH, may be prepared directly by the reaction of a compound of formula (III):

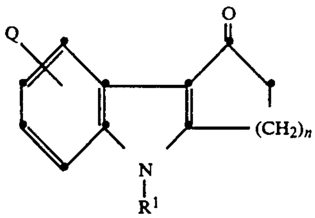

(III)

or a protected derivative thereof, with a compound of formula (IV):

OHC-Im (IV)

or a protected derivative thereof, in the presence of a base such as an alkali metal amide (e.g. lithium diisopropylamide) in an inert solvent such as an ether (e.g. tetrahydrofuran). The dehydration is then performed in situ using the appropriate conditions described above, followed where necessary by deprotection. Compounds of formula (II) may be isolated as intermediates in this particular embodiment of process (A).

According to a further embodiment of this process, a compound of general formula (I), wherein A-B represents the group C═CH, may be prepared by converting the hydroxy group of a compound of formula (II), into a leaving group such as a hydrocarbylsulphonate (e.g. a mesylate or a trifluoromethanesulphonate) using conventional methods, in the presence of a base (e.g. triethylamine or aqueous sodium hydroxide) in a solvent such as an ether (e.g. tetrahydrofuran) or an alcohol (e.g. methanol).

According to another general process (B), a compound of general formula (I) may be converted into another compound of formula (I) using conventional techniques. Such conventional techniques include hydrogeneration, alkylation, acylation and acid-catalysed cleavage using protection and deprotection where necessary.

Thus, according to one embodiment of the interconversion process (B)5 compounds of formula (I) in which A-B represents the group $CH{=}CH_2$ and $R^1$ is other than a $C_{3-6}$ alkenyl or a $C_{3-6}$ alkynyl group, and/or Q is other than a benzyloxy group may be prepared by hydrogenating the corresponding compounds in which A-B represents the group C═CH. Hydrogenation may also be used to convert an alkenyl or an alkynyl substituent into an alkyl substituent or an alkynyl into an alkenyl substituent, or a benzyloxy substituent into a hydroxyl group.

Hydrogenation according to general process (B) may be effected using conventional procedures, for example using hydrogen in the presence of a noble metal catalyst (e.g. palladium, Raney nickel, platinum or rhodium). The catalyst may be supported on, for example, charcoal, alumina or alternatively a homogeneous catalyst such as tris(triphenylphosphine)rhodium chloride may be used. The hydrogenation will generally be effected in a solvent such as an alcohol (e.g. methanol or ethanol), an ether (e.g. dioxan), a halogenated hydrocarbon (e.g. dichloromethane) or an ester (e.g. ethyl acetate) or mixtures thereof, and at a temperature in the range −20° to +100° C., preferably 0° to 50° C.

According to another embodiment of the interconversion process (B), a compound of formula (I) in which $R^1$ represents a $C_{1-6}$ alkyl, $C_{3-7}$ cycloalkyl, $C_{3-6}$ alkenyl, $C_{3-10}$ alkynyl, $C_{3-7}$ cycloalkyl$C_{1-4}$alkyl or phenyl $C_{1-3}$ alkyl group, or a compound in which at least one of $R^2$ and $R^3$ represents a $C_{1-6}$ alkyl, $C_{3-7}$ cycloalkyl, $C_{3-6}$ alkenyl or phenyl $C_{1-3}$ alkyl group or a compound in which Q represents a $C_{1-4}$ alkoxy or a phenyl $C_{1-3}$ alkoxy group or a compound in which $R^7$ and/or $R^8$ represents a $C_{1-4}$ alkyl or $C_{3-4}$ alkenyl group may be prepared by alkylating a compound of formula (I) where one or more of $R^1$, $R^2$, $R^3$, $R^7$ and $R^8$ represent a hydrogen atom, or Q represents a hydroxyl group.

The term 'alkylation' according to general process (B) thus also includes the introduction of other groups such as cycloalkyl, alkenyl or phenalkyl groups.

The above alkylation reactions may be effected using the appropriate alkylating agent selected from compounds of formula $R^9Z$ where $R^9$ represents a $C_{1-6}$ alkyl, $C_{3-7}$ cycloalkyl, $C_{3-6}$ alkenyl, $C_{3-10}$ alkynyl, $C_{3-7}$ cycloalkyl$C_{1-4}$ alkyl, or phenyl$C_{1-3}$alkyl group, and Z represents a leaving atom or group such as a halogen atom (e.g. chlorine, bromine or iodine), an acyloxy group (e.g. trifluoroacetyloxy or acetoxy), or a sulphonyloxy group (e.g. trifluoromethanesulphonyloxy, p-toluenesulphonyloxy or methanesulphonyloxy); or a sulphate of formula $(R^9)_2SO_4$.

The alkylation reaction is conveniently carried out in an inert organic solvent such as a substituted amide (e.g. dimethylformamide), an ether (e.g. tetrahydrofuran) or an aromatic hydrocarbon (e.g. toluene), preferably in the presence of a base. Suitable bases include, for example, alkali metal hydrodes (e.g. sodium hydride), alkali metal amides (e.g. sodium amide or lithium diisopropylamide), alkali metal amides (e.g. sodium carbonate) or an alkali metal alkoxide (e.g. sodium or potassium methoxide, ethoxide or t-butoxide). The reaction may conveniently be effected at a temperature in the range −80° to +100° C., preferably −80° to +50° C.

According to another embodiment of general process (B), a compound of formula (I) wherein $R^1$ represents $-CO_2R^5$, $-COR^5$, $-CONR^5R^6$ or $-SO_2R^5$ may be prepared by acylating a compound of formula (I) wherein $R^1$ represents a hydrogen atom. The acylation reactions may be effected using an appropriate acylating agent according to conventional procedures.

Suitable acylating agents include acyl halides (e.g. an acyl, alkylsulphonyl, or arylsulphonyl chloride, bromide or iodide), mixed and symmetrical anhydrides (e.g. a symmetrical anhydride of formula $(R^5CO)_2O$), lower alkyl haloformates (e.g. lower alkyl chloroformates), sulphonates (e.g. hydrocarbylsulphonates such as p-toluenesulphonate), carbamoyl halides (e.g. carbamoyl chlorides of formula $R^5R^6NCOCl$), carbonates and isocyanates (e.g. isocyanates of formula $R^5NCO$).

The reaction may conveniently be effected in the presence of a base such as an alkali metal hydride (eg. sodium or potassium hydride), an alkali metal carbonate (e.g. sodium or potassium carbonate), an alkali metal alkoxide (e.g. potassium t-butoxide), butyllithium, lithium diisopropylamide or an organic tertiary amine (e.g. triethylamine or pyridine).

Suitable solvents which may be employed in the acylation of general process (B) include amides (e.g. dimethylformamide or dimethylacetamide), ethers (e.g. tetrahydrofuran dioxan), halogenated hydrocarbons (e.g. methylene chloride), nitriles (e.g. acetonitrile) and esters (e.g. ethyl acetate). The reaction may conveniently be effected at a temperature of from −10° to +150° C.

According to a yet further embodiment of general process (B), a compound of formula (I) in which Q represents a hydroxyl group may be prepared from the corresponding compound in which Q represents an alkoxy or benzyloxy group by acid-catalysed cleavage. The reaction may be effected using a Lewis acid such as boron tribromide or aluminium trichloride, in a solvent such as a halogenated hydrocarbon (e.g. dichloromethane). The reaction temperature may conveniently be in the range −80° to +100° C.

According to another general process (C), a compound of general formula (I), wherein A-B represents the group $CH{=}CH_2$, may be prepared by reacting a compound of formula (III) or a protected derivative thereof, with a compound of formula (V):

$$LCH_2\text{-Im} \quad (V)$$

wherein L represents a leaving atom or group, such as a halogen atom or an acyloxy or sulphonyloxy group as previously defined for Z, or a protected derivative thereof, in the presence of a base, followed where necessary by removal of any protecting groups. Suitable bases include alkali metal hydrides (e.g. sodium or potassium hydride), alkali metal alkoxides (e.g. potassium-t-butoxide) or alkali metal amides (e.g. lithium diisopropylamide). The reaction may conveniently be carried out in an inert solvent such as ether (e.g. tetrahydrofuran), a substituted amide (e.g. dimethylformamide), or an aromatic hydrocarbon (e.g. toluene) and at a temperature in the range −80° to +50° C.

According to another general process (D), a compound of general formula (I), wherein A-B represents the group $CH{=}CH_2$, may be prepared by oxidising a compound of formula (VI):

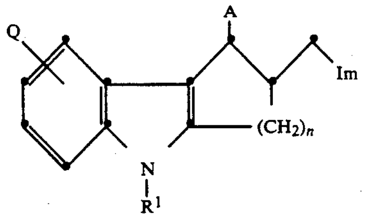

(VI)

wherein A represents a hydrogen atom or hydroxyl group, or a salt or protected derivative thereof, followed where necessary by removal of any protecting groups.

The oxidation process may be effected using conventional methods and the reagents and reaction conditions should be chosen such that they do not cause oxidation of the indole moiety or other functional groups. Thus, the oxidation process is preferably effected using a mild oxidising agent.

When oxidising a compound of formula (VI) in which A represents a hydrogen atom, suitable oxidising agents include quinones in the presence of water (e.g. 2,3-dichloro-5,6-dicyano-1,4-benzoquinone or 2,3,5,6-tetrachloro-1,4-benzoquinone), selenium dioxide, cerium (IV) oxidising reagents (e.g. ceric ammonium nitrate) and chormium (VI) oxidising agents (e.g. a solution of chromic acid in acetone, for example Jones' reagent, or chromium trioxide in pyridine).

When oxidising a compound of formula (VI) in which A represents a hydroxyl group, suitable oxidising agents include quinones in the presence of water (e.g. 2,3-dichloro-5,6-dicyano-1,4-benzoquinone or 2,3,5,6-tetrachloro-1,4-benzoquinone), ketones (e.g. acetone, methylethylketone or cyclohexanone) in the presence of a base (e.g. aluminium t-butoxide), chromium (VI) oxidising agents (e.g. a solution of chromic acid in acetone, for example Jones reagent, or chromium trioxide in pyridine), N-halosuccinimides (e.g. N-chlorosuccinimide or N-bromosuccinimide), dialkylsulphoxides (e.g. dimethylsulphoxide) in the presence of an activating agent such as N,N'-dicyclohexylcarbodiimide or an acyl halide (e.g. oxalyl chloride or tosyl chloride), pyridine-sulphur trioxide complex, and dehydrogenation catalysts (e.g. copper chromite, zinc oxide, copper or silver).

Suitable solvents may be selected from ketones (e.g. acetone or butanone), ethers (e.g. tetrahydrofuran or dioxan), amides (e.g. dimethylformamide), alcohols (e.g. methanol), hydrocarbons (e.g. benzene or toluene), halogenated hydrocarbons (e.g. dichloromethane) and water or mixtures thereof.

The process is conveniently effected at a temperature of −70° to +50° C. It will be understood that the choice of oxidising agent will affect the preferred reaction temperature.

Compounds of formulae (II) and (VI) are novel compounds and constitute a further aspect of the invention.

According to another general process (E), a compound of general formula (I), wherein A-B represents the group $CH{=}CH_2$, may be prepared by cyclising a compound of formula (VII):

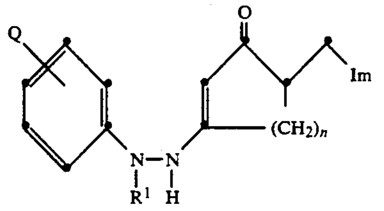

(VII)

or a salt or protected derivative thereof, followed where necessary by removal of any protecting groups.

It will be appreciated that the compounds of formula (VII) may exist in the corresponding enol hydrazone tautomeric form.

The cyclisation may be carried out in aqueous or non-aqueous media, in the presence of an acid catalyst. When an aqueous medium is employed this may be water or an aqueous organic solvent such as an aqueous alcohol (e.g. methanol, ethanol or isopropanol) or an aqueous ether (e.g. dioxan or tetrahydrofuran) as well as mixtures of such solvents and the acid catalyst may be, for example, an inorganic acid such as concentrated hydrochloric or sulphuric acid. (In some cases the acid catalyst may also act as the reaction solvent). In an anhydrous reaction medium, which may comprise one or more alcohols or ethers (e.g. as described above), carboxylic acids (e.g. acetic acid) or esters (e.g. ethyl acetate), the acid catalyst will generally be a Lewis acid such as boron trifluoride, zinc chloride or magnesium chloride. The cyclisation reaction may conveniently be carried out at temperatures of from 20° to 200° C. preferably 50° to 125 ° C.

Alternatively the process may be carried out in the presence of polyphosphate ester in a reaction medium which may comprise one or more organic solvents, preferably halogenated hydrocarbons such as chloroform, dichloromethane, dichloroethane, dichlorodifluoromethane, or mixtures thereof. Polyphosphate ester is a mixture of esters which may be prepared from phosphorus pentoxide, diethylether and chloroform according to the method described in 'Reagents for Organic Synthesis', (Fieser and Fieser, John Wiley and Sons 1967).

According to a particular embodiment of process (E), a compound of general formula (I) may be prepared directly by the reaction of a compound of formula (VIII):

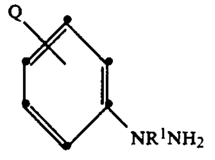

(VIII)

or a salt thereof, with a compound of formula (IX):

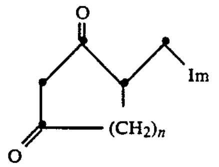

(IX)

or a protected derivative thereof, using the appropriate conditions as described above, followed where necessary by removal of any protecting groups. Compounds of formula (VII) may be isolated as intermediates in this particular embodiment.

A protected derivative of formula (IX) may for example have one or both of the carbonyl groups protected (e.g. as an enol ether). It will be appreciated that when a compound of formula (IX) is used in which the carbonyl group at the 3-position is protected, it may be necessary to remove the protecting group in order for reaction to occur with the compound of formula (VIII). Deprotection may be carried out by conventional methods, as described hereinafter. If desired, deprotection may be effected in situ.

It should be appreciated that in the above transformations it may be necessary or desirable to protect any sensitive groups in the molecule of the compound in question to avoid undesirable side reactions. For example, it may be necessary to protect the keto group, for example, as a ketal or a thioketal or as an enol ether. It may also be necessary to protect the carbazolone and/or imidazole nitrogen atoms, for example with an arylemthyl (e.g. benzyl or trityl), alkyl (e.g. t-butyl), alkoxymethyl (e.g. methoxymethyl), acyl (e.g. benzyloxycarbonyl) or a sulphonyl (e.g. N,N-dimethylaminosulphonyl or p-toluenesulphonyl) group. When Q represents a hydroxyl group it may be necessary to protect the hydroxyl group, for example with an arylemthyl (e.g. benzyl or trityl) group.

Thus according to another general process (F), a compound of general formula (I) may be prepared by the removal of any protecting groups from a protected form of a compound of formula (I). Deprotection may be effected using conventional techniques such as those described in 'Protective Groups in Organic Synthesis' by Theodora W. Greene (John Wiley and Sons, 1981).

For example a ketal such as an alkyleneketal group may be removed by treatment with a mineral acid such as hydrochloric acid. A thioketal group may be cleaved by treatment with a mercuric salt, (e.g. mercuric chloride), in a suitable solvent, such as ethanol. An enol ether may be hodrolysed in the presence of an aqueous acid (e.g. dilute sulphuric or hydrochloric acid). An arylemthyl N-protecting group may be cleaved by hydrogenolysis in the presence of a catalyst (e.g. palladium on charcoal) and a trityl group may also be cleaved by acid hydrolysis (e.g. using dilute hydrochloric or actic acid). An alkoxyalkyl group may be removed using a Lewis acid such as boron tribromide. An acyl group may be removed by hydrolysis under acidic or basic conditions (e.g. using hydrogen bromide or sodium hydroxide). A sulphonyl group may be removed by alkaline hydrolysis. An arylemthyl OH-protecting group may be cleaved under acidic conditions (e.g. with dilute acetic acid, hydrobromic acid or boron tribromide) or by hydrogenolysis in the presence of a catalyst (e.g. palladium on charcoal).

Compounds of formula (II) may be prepared by condensing a compound of formula (III), or a protected derivative thereof, with a compound of formula (IV), or a protected derivative thereof, in the presence of a base such as an alkali metal amide (e.g. lithium diisopropylamide) in an inert solvent such as an ether (e.g. tetrahydrofuran).

Compounds of formula (III) may be prepared, for example, by the method or methods analogous to that described by Oikawa and Yonemitsu in *J. Org. Chem.*, 1977, 42, 1213.

Compounds of formula (IV) may be prepared, for example, by oxidation of the corresponding hydroxymethylimidazole of formula (XI):

$$HOCH_2\text{-}Im \qquad (XI)$$

or a protected derivative thereof, with an oxidising agent such as manganese dioxide.

Compounds of formula (V) in which L represents a halogen atom may be obtained by reacting a compound of formula (XI), or a protected derivative thereof, with a halogenating agent such as thionyl chloride or a phosphorus trihalide (e.g. phosphorus trichloride). Compounds of formula (V) in which L represents an acyloxy group or a sulphonyloxy group may be prepared by reacting a compound of formula (XI) with an appropriate acylating or sulphonylating agent such as an anhydride or a sulphonyl halide (e.g. methanesulphonyl chloride), optionally in the presence of a base (e.g. triethylamine or pyridine).

Compounds of formula (VI) may be prepared, for example, by reacting a compound of formula (I) with an appropriate reducing agent. Thus a compound of formula (VI) wherein A represents a hydrogen atom may be prepared by reacting a compound of formula (I) with a hydride reducing agent such as diisobutylaluminium hydride, or sodium borohydride. When diisobutylaluminium hydride is used, it may be necessary to follow the reaction with an additional hydrogenation step.

Hydrogenation may be effected using conventional procedures, for example, as described in process (B). A compound of formula (VI) wherein A represents a hydroxyl group may be prepared, for example, by reacting a compound of formula (I) with an alkali metal hydride (e.g. lithium hydride).

Compounds of formula (VII) may be prepared, for example, by the reaction of a compound of formula (VIII) or a salt thereof, with a compound of formula (IX), or a protected derivative thereof, in a suitable solvent such as an alcohol, and at a temperature of, for example, from 20° to 100° C.

Compounds of formula (IX) may be prepared by reacting a compound of formula (V), or a protected derivative thereof, with the appropriate 1,3-diketone, or a protected derivative thereof, under the conditions referred to in process (C) above.

Compounds of formulae (VIII) and (XI) are either known or may be prepared from known compounds by conventional procedures.

Where it is desired to isolate a compound of the invention as a salt, for example a physiologically acceptable salt, this may be achieved by reacting the compound of formula (I) in the form of the free base with an appropriate acid, preferably with an equivalent amount, in a suitable solvent such as an alcohol (e.g. ethanol or methanol), an aqueous alcohol (e.g. aqueous ethanol), an ester (e.g. ethyl acetate) or an ether (e.g. tetrahydrofuran).

Physiologically acceptable salts may also be prepared from other salts, including other physiologically acceptable salts, of the compound of formula (I) using conventional methods.

Individual enantiomers of the compounds of the invention may be obtained by resolution of a mixture of enantiomers (e.g. a racemic mixture) using conventional means, such as an optically active resolving acid; see for example 'Stereochemistry of Carbon Compounds' by E.L. Eliel (McGraw Hill 1962) and 'Tables of Resolving Agents' by S. H. Wilen.

Examples of optically active resolving acids that may be used to form salts with the racemic compounds include the (R) and (S) forms of organic carboxylic and sulphonic acids such as tartaric acid, di-p-toluoyltartartic acid, camphorsulphonic acid and lactive acid. The resulting mixture of isomeric salts may be separated, for example, by fractional crystallisation into the diastereoisomers and if desired, the required optically active isomer may be converted into the free base.

The methods indicated above for preparing the compounds of the invention can be used as the last main step in the preparative sequence. The same general methods can be used for the introduction of the desired groups at an intermediate stage in the stepwise formation of the required compound, and it will be appreciated that these general methods can be combined in different ways in such multi-stage processes. The sequence of the reactions in multi-stage processes should of course be chosen so that the reaction conditions used do not affect groups in the molecule which are desired in the final product.

The invention is further illustrated by the following Examples. All temperatures are in ° C. Thin layer chromatography (t.l.c.) was carried out on silica, and flash column chromatography (FCC) and short-path column chromatography (SPCC) on silica (Merck 9385 and Merck 7747 respectively). Solvent System A as used for chromatography denotes dichloromethane:ethanol:0.88 ammonia solution. $^1$H-N.m.r. spectra were obtained at 250 MHz (integration, multiplicity); multiplicity legend: s=singlet, d=doublet, t=triplet, m=multiplet, br=broad. Organic extracts were dried over magnesium sulphate or sodium sulphate. The following abbreviations are used: THF - tetrahydrofuran; DMF - dimethylformamide; IMS - industrial methylated spirits.

INTERMEDIATE 1

5-Methyl-1-(triphenylmethyl)-1H-imidazole-4-methanol

A solution of triphenylchloromethane (13.1 g) in dry DMF (80 ml) was added dropwise over 30 min. to a stirred solution of 4-methyl-5-imidazolemethanol hydrochloride (7.0 g) and triethylamine (9.52 g) in dry DMF (75 ml) at room temperature under nitrogen, and stirring was continued for 2.5 h. The suspension was poured onto ice (600 ml), stirred for 30 min. and filtered. The resulting solid (12.0 g) was triturated twice with acetone (2×250 ml) to give the title compound (8.4 g), t.l.c. (System A 94.5:5:0.5) Rf 0.19.

INTERMEDIATE 2

5-Methyl-1-(triphenylmethyl)-1H-imidazole-4-carboxaldehyde

A mixture of 5-methyl-1-(triphenylemthyl)-1H-imidazole-4-methanol (4.0 g), manganese dioxide (activated) (40 g) and dioxan (225 ml) was stirred at room temperature overnight. The suspension was filtered and the solide was washed with hot chloroform (1 l). The combined filtrates were evaporated in vacuo to leave a solid (4.0 g) which was purified by FCC eluting with chloroform to give a solid which was triturated with hexane (ca. 50 ml) to give the title compound (2.99 g), m.p. 184°-188° (decomp.).

INTERMEDIATE 3

1,2,3,9,-Tetrahydro-3-[hydroxy[5-methyl-1-(triphenylmethyl)-1H-imidazol-4-yl]methyl]-9-methyl-4H-carbazol-4-one n-Butyllithium (1.57 M; 1.08 ml) was added at −78° under nitrogen with stirring to a solution of diisopropylamine (0.24 ml) in dry THF (7 ml) and stirred at 0° for 30 min. The solution was cooled to −78° and added via a cannula to 1,2,3,9-tetrahydro-9-methyl-4H-carbazol-4-one (282 mg) at −78° under nitrogen with stirring. After 1 h at −78 °, followed by 1 h at 0°, the mixture was cooled to −78° and treated with Intermediate 2 (500 mg) in THF (6 ml). After 4 h at −78°, the mixture was allowed to warm to 23° and stirred for 14 h. The resultant solide (the reaction mixture had evaporated) was cooled to −78° treated with THF (10 ml), followed by acetic acid (1 ml), warmed to 0°, and poured into aqueous saturated sodium bicarbonate (50 ml). The mixture was extracted with dichloromethane (2×60 ml) and the combined, dried organic extracts were evaporated. The residue was purified by SPCC eluting with System A (967:30:3) to give the title compound (280 mg), m.p. 141°-147°.

INTERMEDIATE 4

3-(3-Fluorophenylhydrazono)-1-cyclohexan-1-ol

3-Fluorophenylhydrazine hydrochloride (9.35 g) in water (100 ml) was treated with 2 N aqueous sodium hydroxide (29 ml) and the resultant solution was added over 2 h to a stirred solution of cyclohexan-1,3-dione (6.65 g) in water (100 ml) under nitrogen. This mixture was stirred for 18 h and the resultant precipitate was filtered off and then stirred with water (150 ml). The solid was again filtered off, washed with water (50 ml) and dried to give a powder (9.90 g). This was washed with hexane (2×200 ml) and the solide was collected to give the title compound (5.3 g), m.p. 142°-144°.

INTERMEDIATE 5

7-Fluoro-1,2,3,9-tetrahydro-4H-carbazol-4-one

A mixture of glacial acetic acid (25 ml), 3-(3-fluorophenylhydrazono)-1-cyclohexen-1-ol (1.1 g) and fused zinc chloride (1.0 g) was heated at 100° for 20 h. The cooled reaction mixture was poured into water (35 ml) and extracted with dichloromethane (2×30 ml). The combined, dried organic extracts were evaporated to give an oil which was purified by SPCC eluting with ethyl acetate:hexane (3:2) to give the title compound (0.15 g) as a powder, m.p. 231°-233°.

INTERMEDIATE 6

7-Fluoro-1,2,3,9-tetrahydro-9-methyl-4H-carbazol-4-one

A solution of 7-fluoro-1,2,3,9-tetrahydro-4H-carbazol-4-one (1.0 g) in dry DMF (8 ml) was added dropwise to a stirred, ice-cooled suspension of pre-washed (hexane: 2×10 ml) sodium hydride (78% dispersion in oil; 175 mg) in dry DMF (5 ml) under nitrogen and stirring was continued at room temperature for 1.5 h. The solution was cooled to 0°, iodomethane (0.35 ml) was added dropwise and stirring was continued at 0° for 2 h. The suspension was poured into 8% aqueous sodium bicarbonate (30 ml) extracted with dichloromethane (2×30 ml) and the combined, dried organic extracts were evaporated and dried in vacuo at 100° for 18 h to give the title compound (1.03 g) as a solide, m.p. 174°-175°.

INTERMEDIATE 7

1,2,3,9-Tetrahydro-3-[(5-methyl-1-(triphenylmethyl)-1H-imidazol-4-yl) methyl]-4H-carbazol-4-one A solution of triphenylchloromethane (4.2 g) in dry DMF (40 ml) was added dropwise to a solution of 1,2,3,9-tetrahydro-3-[(5-methyl-1H -imidazol-4-yl)methyl]-4H-carbazol-4-one (3.5 g) and triethylamine (1.75 ml) in dry DMF (35 ml) under nitrogen. After stirring for 4 h the mixture was poured into water (300 ml) and extracted with dichloromethane (3×100 ml). The combined extracts were washed with water (200 ml), dried and evaporated to give an oil (ca. 9 g) which was purified by FCC eluting with System A (200:10:1) to give the title compound (4.57 g) as a foam, t.l.c. (System A 200:10:1) RF 0.32.

INTERMEDIATE 8

4-(Chloromethyl)-5-methyl-1-(triphenylmethyl)-1H-imidazole

A solution of thionyl chloride (1.3 ml) in dry dichloromethane (10 ml) was added over 5 min. to a stirred suspension of 5 -methyl-1-(triphenylemthyl) -1H-imidazole-4-methanol (5.0 g) in a mixture of dichloromethane (100 ml) and dry DMF (2 ml) at 0°. The mixture was stirred at 0° for 30 min. and washed consecutively with 8% sodium bicarbonate (2×50 ml), water (50 ml), dried and evaporated in vacuo below 40° to give an oil (5 g). This was dissolved in ether (100 ml) and the resulting solution was filtered through a pad of silica which was further eluted with ether (2×100 ml). The combined filtrates were evaporated below 40° to give a foam which was triturated with cold hexane and filtered to give the title compound (4.2 g) as a solid, m.p. 133°-135°.

INTERMEDIATE 9

3-Methoxy-6-[[5-methyl-1-(triphenylmethyl)-1H-imidazol-4-yl]methyl]-2-cyclohexen-1 -one n-Butyllithium (1.58 M in hexane; 21 ml) was added at −78° under nitrogen to a stirred solution of diisopropylamine (4.6 ml) in dry THF (75 ml) and the solution was stirred at 0° for 30 min. The solution was cooled to −78° and added to a solution of 3-methoxy-2-cyclohexen-1 one (3.4 g) in dry THF (25 ml) at −78° under nitrogen with stirring. After stirring for 1 h at −78° and for 30 min. at 0° the solution was cooled to −78° and a solution of 4-(chloromethyl)-5-methyl-1 -(triphenylmethyl)-1H-imidazole (10 g) in dry THF (100 ml) was added dropwise with stirring under nitrogen. The solution was stirred at −78° for 3 h and at 0° for 30 min., treated with 8% aqueous sodium bicarbonate (400 ml) and extracted with ethyl acetate (2×300 ml). The combined, dried organic extracts were evaporated to give an oil (ca. 13 g) which was purified by SPCC eluting with System A (967:30:3) to give the title compound (3.28 g), m.p. 145°-148°.

INTERMEDIATE 10

1,2,3,9-Tetrahydro-3-[[(5-methyl-1-(triphenylmethyl)-1H-imidazol-4-yl) methyl]-9-(phenylmethyl)-4H-carbazol-4-one A solution of 1,2,3,9-tetrahydro-3-[[5-methyl-1-(triphenylmethyl) -1H-imidazol-4-yl]methyl]-4H-carbazol-4-one (500 mg) in dry DMF (3 ml) was added dropwise to a stirred suspension of sodium hydride (73% dispersion in oil; 38 mg) in dry DMF (1 ml) under nitrogen. After 20 min. benzyl bromide (0.14 ml) was added and the mixture was stirred for 3 h. Water (50 ml) was added and the suspension was extracted with dichloromethane (3×25 ml). The combined, dried organic extracts were evaporated to give an oil (ca. 850 mg) which was purified by FCC (column made up in ethyl acetate:hexane:-triethylamine 79:20:1) eluting with ethyl acetate: hexane (4:1) to give the title compound (265 mg) as a solid, m.p. 78°-80°.

INTERMEDIATE 11

9-(Cyclopentylmethyl)-1,2,3,9-tetrahydro-3-[[5-methyl-1-(triphenylmethyl) -1H-imidazol-4-yl]methyl]-4H-carbazol-4-one Using the procedures described above for Intermediate 10, 1,2,3,9-tetrahydro-3-[[5-methyl-1(triphenylmethyl)-1H-imidazol-4-yl]methyl]-4H -carbazol-4-one (500 mg) was treated with sodium hydride (73% dispersion in oil; 38 mg) and was then stirred with cyclopentanemethanol (p-toluenesulphonate) (292 mg) for 24 h. Work up and FCC as described above gave the title compound (283 mg), m.p. 177°-179°.

INTERMEDIATE 12

1,2,3,9-Tetrahydro-3-[[5-methyl-1-(triphenylmethyl)-1H-imidazol-4-yl]methyl ]-9-(2-propynyl)-4H-carbazol-4-one Propargyl bromide (0.086 ml) was added to a suspension of 1,2,3,9-tetrahydro-3-[[5-methyl-1-(triphenylmethyl)-1H-imidazol-4-yl]methyl ]-4H-carbazol-4-one (500 mg) and potassium carbonate (265 mg) in acetone (10 ml) and the mixture was stirred under nitrogen for 60 h. More propargyl bromide (0.086 ml) was added and the mixture was stirred at room temperature for 24 h and then at reflux for 6 h. Water (50 ml) was added and the suspension was extracted with dichloromethane (3×25 ml). The combined, dried organic extracts were evaporated to give a gum (650 mg) which was purified by FCC (column made up in ethyl acetate:hexane:triethylamine 80:19:1) eluting with ethyl acetate:hexane (4:1) to give the title compound (95 mg) as a foam, t.l.c. on $Et_3N$ impregnated $SiO_2$ (ethyl acetate:hexane 4:1) Rf 0.30.

INTERMEDIATE 13

1,2,3,9-Tetrahydro-9-methyl-3-[(5-methyl-1H-imidazol-4-yl)methyl]4H-carbazole maleate A suspension of 1,2,3,9-tetrahydro-3-[(5-methyl-1H-imidazol-4-yl) methyl]-9methyl-4H-carbazol-4-one (0.5 g) in dry dichloromethane (150 ml) at −57° under nitrogen was treated with a solution of diisobutylaluminium hydride (1.0 M in cyclohexane; 6 ml) and the mixture was stirred for 4 h while warming to 5°. Methanol (5 ml) was added and the mixture was stirred for a further 1 h and was then filtered. The gelatinous precipitate was further washed with dichloromethane (50 ml) and the combined filtrates were evaporated in vacuo. The residual oil (ca. 0.55 g) was purified by FCC eluting with System A (95:5:0.5) to give a solid (198 mg). A mixture of this solid (175 mg) in ethanol (15 ml) was hydrogenated at room temperature and atmospheric pressure over a stirred suspensions of pre-reduced 10% palladium on carbon (50% aqueous paste; 20 mg) in ethanol (10 ml) for 4 h. The mixture was filtered, evaporated in vacuo, and the residual gum was partitioned between 0.2 N hydrochloric acid (20 ml) and dichloromethane (20 ml; discarded). The acidic layer was basified (2 N sodium hydroxide) and extracted with chloroform (3×20 ml). These latter chloroform layers were dried and evaporated in vacuo to leave a gum (155 mg) which was dissolved in dichloromethane:methanol (1:1) (15 ml) and treated with a solution of maleic acid (65 mg) in methanol (0.3 ml). Concentration in vacuo to ca. 2 ml and dilution with dry ether afforded the title compound (176 mg) as a solid, m.p. 175°-179° (decomp.).

INTERMEDIATE 14

1,2,3,9-Tetrahydro-9-methyl-3-[[5-methyl-1-(triphenylmethyl)-1H-imidazol-4-yl]methyl ]-4H-carbazol-4-one A solution of triphenylchloromethane (286 mg) in dry DMF (10 ml) was added dropwise to a stirred solution of 1,2,3,9-tetrahydro-9-methyl-3-[(5-methyl-1H-imidazol-4-yl)methyl]-4H-carbazol-4-one (292 mg) and triethylamine (101 mg) in dry DMF (20 ml) and the resulting solution was stirred at room temperature under nitrogen for 3.5 h. The reaction mixture was then poured into water (100 ml) and the resultant suspension was extracted with dichloromethane (3×50 ml). The combined, dried organic extracts were adsorbed onto FCC silica which was then applied to a column and FCC eluting with System A (150:8:1) gave a solid which was further purified by crystallisation from dichloromethane:hexane (2:1) to give the title compound (304 mg), m.p. 193°-195°.

INTERMEDIATE 15

N,N,5-Trimethyl-4-[(2,3,4,9-tetrahydro-9-methyl-4-oxo-1H-carbazol-3-yl) methyl]-1H-imidazole-1-sulphonamide A solution of dimethylsulphamoyl chloride (0.16 ml) in dry dichloromethane was added to a stirred solution of 1,2,3,9-tetrahydro-9-methyl -3-[(5-methyl-1H-imidazol-4-yl)methyl]-4H-carbazol-4-one (438 mg) and triethylamine (0.25 ml) in dry dichloromethane (30 ml) and the mixture was heated at reflux for 18 h. After cooling the reaction mixture was adsorbed onto FCC silica which was then applied to a column and FCC eluting with System A (150:8:1) gave an oil, which solidified to a powder on trituration with dry hexane (30 ml). This powder was then further purified by dissolution in dry dichloromethane (30 ml) and crystallisation by addition of dry hexane (10 ml) to give the title compound (518 mg), m.p. 122°-124°.

INTERMEDIATE 16

1,2,3,9-Tetrahydro-3-[[1-(methoxymethyl)-5-methyl-1H-imidazol-4yl]-methyl]-9-methyl-4 H-carbazol-4-one and 1,2,3,9-tetrahydro-3-[[1-(methoxymethyl) -4-methyl-1H-imidazole-5-yl]methyl]-9-methyl-4H-carbazol-4-one (4:1)

A solution of chloromethyl methyl ether (0.22 ml) in chloroform (10 ml) was added to a stirred solution of 1,2,3,9-tetrahydro -3-[(5-methyl-1H-imidazol-4-yl)methyl]-9-methyl-4H-carbazol -4-one (0.44 g) and triethylamine (0.5 ml) in chloroform (30 ml) under nitrogen. The resulting solution was stirred at 20° for 2 h and partitioned between chloroform (25 ml) and 2 N sodium bicarbonate solution (2×30 ml). The dried organic extract was evaporated and the residue (0.45 g) was purified by FCC eluting with System A (200:8:1) to give the title compounds (0.25 g) as a gum, t.l.c. (System A 75:8:1) RF 0.5. N.m.r. ($CDCl_3$) showed the title compounds to be in the ratio of 4:1.

INTERMEDIATE 17

Phenylmethyl 5-methyl-4-(2,3,4,9-tetrahydro-9-methyl-4-oxo-1H -carbazol-3-yl)methyl]-1H-imidazole-1-carboxylate and phenylmethyl 4-methyl-5-[2,3,4,9-tetrahydro-9-methyl-4-oxo-1H-carbazol-3-yl) methyl]-1H-imidazole-1-carboxylate (97:3)

A solution of carbobenzoxy chloride (0.25 ml) in chloroform (10 ml) was added to a stirred solution of 1,2,3,9-tetrahydro-3-[(5-methyl-1H-imidazol -4-yl)methyl]-methyl-4H-carbozol-4-one (0.44 g) and triethylamine (0.25 ml) in chloroform (30 ml) under nitrogen. The resulting solution was stirred at 20° for 2 h and partitioned between chloroform (25 ml) and 2 N sodium Bicarbonate solution 92×30 ml). The organic extract was dried and evaporated to leave a gum (0.8 g) which was purified by FCC eluting with System A (200:8:1) to give a solid (0.64 g) which was crystallised from ethanol (3 ml) to give the title compounds (0.62 g), t.l.c. (System A 200:8:1) RF 0.47. N.m.r. ($CDCl_3$) showed the title compound to be in the ratio of 97:3.

INTERMEDIATE 18

3-(2-Fluorophenyl)amino]-2-cyclohexen-1-one

2-Fluorophenyl (10 g) and cyclohexane-1,3,-dione (10 g) were heated together under nitrogen at 120° For 1 h. The cooled mixture was triturated with ether and filtered to give the title compound (14.8 g), m.p. 116°-118°.

INTERMEDIATE 19

8-Fluoro-1,2,3,9-tetrahydro-4H-carbazol-4-one

3-[(2-Fluorophenyl)amino]-2-cyclohexen-1-one (14.8 g), palladium (II) acetate (1 g), and copper (II) acetate (29.5 g) were heated together in DMF (100 ml) under nitrogen at 140° for 2 h. The solvent was removed in vacuo, and the residue was purified by FCC eluting with ether to give the title compound (10.1 g), m.p. 222°-224°.

INTERMEDIATE b 20

8-Fluoro-9-methyl-1,2,3,9tetrahydro-4H-carbazol-4-one

To a suspension of sodium hydride (80% dispersion in oil; 1.15 g) in dry THF (50 ml) under nitrogen was added 8-fluoro-1,2,3,9-tetrahydro-4H -carbazol-4-one (6.5 g) in dry THF (50 ml), and the mixture was stirred for 1 h. Methyl iodide (4.1 ml) was added, and the mixture was stirred for 3 h. The mixture was then poured into brine (300 ml) and extracted with ether (2×300 ml). The combined, dried organic extracts were evaporated in vacuo to give the title compound (5.77 g), m.p. 126°-128°.

INTERMEDIATE b 21

8-Fluoro-1,2,3,9-tetrahydro-3-[(5-methyl-1H-imidazol-4-yl)methylene-4H-carbazol-4-one Diisopropylamine (3.83 ml) in dry THF (20 ml) was cooled to 0° under nitrogen. n-Butyllithium (1.69 M solution in hexane; 16.3 ml) was added, and the mixture was stirred for 15 min. before cooling to −78°. 8-Fluoro-1,2,3,9-tetrahydro-4H-carbazol-4-one (2.32 g) in dry THF (40 ml) was cooled to −78° under nitrogen, the lithium diisopropylamide solution was added, and the resulting suspension was stirred for 1 h. Intermediate 2 (4.02 g) in dry THF (40 ml) was added, and the mixture was stirred at −78° for 1 h, then warmed to 20° and stirred for 3 h. Methanesulphonic acid (20 ml) and acetic acid (30 ml) were added, and the mixture was heated to 80° for 1 h. The cooled mixture was poured into aqueous potassium carbonate solution (500 ml) and extracted with ethyl acetate (3×50 ml). The combined, dried organic extracts were evaporated in vacuo to leave an oil which was purified by FCC eluting with System A (75:8:1) to give the title compound (723 mg), m.p. 235°-237° (decomp.).

INTERMEDIATE b 22

8-Fluoro-1,2,3,9-tetrahydro-9methyl-3-[(5-methyl-1H-imidazol-4-yl)methylene]-4H-carbazol-4-one Diisopropylamine (2.35 ml) in dry THF (15 ml) was cooled to −78° under nitrogen. n-Butyllithium (124 M solution in hexane; 13.4 ml) was added, and the mixture was stirred for 15 min. before cooling to −78°. 8-Fluoro-9-methyl-1,2,3,9-tetrahydro-4H-carbazol-4-one (3 g) in dry THF (70 ml) was cooled to −78° under nitrogen, the lithium diisopropylamide solution was added, and the resulting mixture was warmed to −40° over 1 h, before re-cooling to −78°. Intermediate 2 (4.9 g) in dry THF (50 ml) was added slowly, and the mixture was allowed to warm to 0° over 3 h. The mixture was re-cooled to −78, acetic acid (20 ml) was added, followed by methanesulphonic acid (50 ml), and the mixture was warmed to 20° and then heated at reflux for 12 h. The cooled mixture was poured into water (400 ml), basified (to pH10) with potassium carbonate (50 g) and extracted with ethyl acetate (3×400 ml). The combined, dried organic extracts were evaporated in vacuo to give an oil which was purified by FCC eluting with System A (100:8:1) to give the title compound (2.79 g), m.p. 260°-264° (decomp.). diisopropylamide solution was added, and the resulting mixture was warmed to −40° over 1 h, before re-cooling to −78°. Intermediate 2 (4.9 l) in dry THF (50 ml) was added slowly, and the mixture was allowed to warm to 0° over 3 h. The mixture was re-cooled to −78°, acetic acid (20 ml) was added, followed by methanesulphonic acid (50 ml), and the mixture was warmed to 20° and then heated at reflux for 12 h. The cooled mixture was poured into water (400 ml), basified (to pH10) with potassium carbonate (50 g) and extracted with ethyl acetate (3×400 ml). The combined, dried organic extracts were evaporated in vacuo to give an oil which was purified by FCC eluting with System A (100:8:1) to give the title compound (2.79 g), m.p. 260°–264° (decomp.).

EXAMPLE 1

(E)-1,2,3,9-Tetrahydro-9-methyl-3[(5-methyl-1H-imidazol-4-yl) methylene]-4H-carbazol-4-one maleate A solution of 1,2,3,9-tetrahydro-3-[hydroxy[5-methyl-1-(triphenylmethyl)-1H-imidazol-4-yl]methyl]-9methyl-4H-carbazol-4-one (2.70 g) in glacial acetic acid (100 ml) was treated with p-toluenesulphonic acid monohydrate (10.80 g) and the stirred solution heated at reflux for 4 h. The cool, dark liquid was evaporated, treated with aqueous saturated sodium bicarbonate (250 ml) and extracted into ethyl acetate (4×250 ml). The combined, dried organic extracts were evaporated, and purified by SPCC. Elution with System A (978:20:2→945:50:5) afforded the free base of the title compound as a light yellow-brown solid (488 mg). A hot solution of the free base (87 mg) in ethanol (ca. 16 ml) was treated with a hot solution of maleic acid (38 mg) in ethanol (1 ml), and on cooling the precipitate was collected to give the title compound (81 mg), m.p. 205°–209°.

Analysis Found: C,65.1; H,5.2; N,10.2;

$Ch_{18}H_{17}N_3O.C_4H_4O_4$ requires C,64.9; H,5.2;N,10.3%.

EXAMPLE 2

(E)-1,2,3,9-Tetrahydro-3-[(5-methyl-1H-imidazol-4-yl)methylene]-4H-carbazol-4-one Lithium diisopropylamide mono(tetrahydrofuran)(1.5 M in cyclohexane; 45 ml) was added dropwise to a cold (−70°) solution of 1,2,3,9-tetrahydro-4H-carbazol-4-one (5.0 g) in dry THF (500 ml) under nitrogen. The solution was stirred at −70° for 1 h whereupon Intermediate 2 (10 g) was added and the mixture was allowed to reach room temperature over 3 h. It was then cooled to −70° and acetic acid (80 ml) followed by p-toluenesulphonic acid (51.4 g) were added. The resulting solution was heated at reflux for 20 h and the solvent was removed in vacuo. The residue was treated with 8% sodium bicarbonate solution (2 l) and extracted with dichloromethane (3×1 l). The combined, dried organic extracts were evaporated to give a gum (ca. 20.8 g) which was purified by FCC eluting with System A (100:10:1) to give the title compound (5.2 g), t.l.c. (System A 100:10:1) Rf 0.35.

$^1$H-N.M.r. ($d_4$-methanol) δ2.39(3H,s), 3.09(2H,t), 3.50(2H,brt), 7.15–7.25 (2H,m), 7.33–7.43(1H,m), 7.53(1H, brs), 7.69(1H,s), 8.10–8.18(1H,m).

EXAMPLE 3

(E)-7-Fluoro1,2,3,9-tetrahydro-9-methyl-3-[(5-methyl-1H-imidazol -4-yl)methylene]-4H-carbazol-4-one Lithium diisopropylamide mono(tetrahydrofuran)(1.5 M in cyclohexane; 3.3 ml) was added dropwise over 10 min. at −70° under nitrogen to a stirred suspension of 7-fluoro-1,2,3,9-tetrahydro-9-methyl-4H-carbazol-4-one (975 mg) in dry THF (30 ml). After 1.5 h a suspension or Intermediate 2 (1.74 g) in dry THF (10 ml) was added and the suspension was stirred at −10° for 2 h. The resultant solution was cooled to −70° and acetic acid (12 ml) was added. The solution was then allowed to warm to −10° and p-toluenesulphonic acid monohydrate (5.8 g) was added and the solution was stirred at reflux for 20 h. It was then cooled and evaporated and the residue was partitioned between 8% aqueous sodium bicarbonate (100 ml) and dichloromethane (70 ml). The suspension was filtered and the resultant solid (1.02 g) was crystallised from methanol (100 ml) to give the title compound (366 mg), m.p. 290°–295°.

Analysis Found: C,69.9; H,5.2; N, 13.2;

$C_{18}H_{16}FN_3O$ requires C,69.9; H,5.2; N,13.6%.

EXAMPLE 4

(E)-1,2,3,9-Tetrahydro-6-methoxy-3-[(5-methyl-1H-imidazol-4-yl) methylene]-4H-carbazol-4-one n-Butyllithium (1.39 M in hexane; 5.0 ml) was added dropwise to a cold (−70°) stirred solution of diisopropylamine (0.98 ml) in dry THF (10 ml) under nitrogen. The solution was stirred at 0° for 30 min, cooled to −70° and added dropwise to a cold (−70°) stirred solution of 1,2,3,9-tetrahydro-6- methoxy-9-methyl-4H-carbazol-4-one (640 mg) in dry THF (20 ml) under nitrogen and the resultant solution was allowed to reach 0° over 1 h. It was then cooled to −70° and a suspension of Intermediate 2 (985 mg) in dry THF (10 ml) was added dropwise and the stirred mixture was allowed to reach room temperature over 3 h. It was then cooled to −70° and was treated with acetic acid (8 ml) followed by p-toluenesulphonic acid (5.3 g) and heated at reflux for 16 n. The solvent was removed in vacuo and the residue treated with 8% sodium bicarbonate solution (150 ml) and extracted with dichloromethane (4×50 ml). The combined, dried organic extracts were evaporated to give a gum (ca. 2 g) which was purified by FCC eluting with System A (200:10:1) to give the title compound (220 mg) as a solid, m.p. 133°–135°, t.l.c. (System A 200:10:1) Rf 0.24.

EXAMPLE 5

(Z)-6,7,8,9-Tetrahydro-5-methyl-9-[(5-methyl-1H-imidazol-4-yl) methylene]cyclohept[b]indol-10(5H)-one maleate A solution of lithium diisopropylamide (1.5 M in cyclohexane; 3.2 ml) was added to a cold (−70°) stirred suspension of 5-methyl-6,7,8,9-tetrahydrocyclohept[-b]indol-10(5H)-one (0.96 g) in dry THF (30 ml) under nitrogen. The resulting solution was stirred at −70° for 15 min. and then at 20° for 30 min., cooled to −70° and treated with a solution of Intermediate 2 (1.6 g) in THF (30 ml). The reaction mixture was then stirred at −70° for 30 min., at 20° for 1 h, cooled to −70° and treated with acetic acid (25 ml). The resulting solution was heated on a steam bath for 1 h and concentrated in vacuo to ca. 10 ml and partitioned between saturated potassium carbonate solution (90 ml) and ethyl acetate (3×90 ml). The combined, dried organic extracts were evaporated to leave a gum (ca. 2 g) which was dissolved in THF (100 ml) and treated with p-toluenesulphonic acid monhydrate (8.5 g) at 100° for 3 h. The resultant solution was concentrated in vacuo to ca. 5 ml and partitioned between ethyl acetate (3×90 ml) and saturated potassium carbonate (90 ml). The combined, dried organic extracts were evaporated to leave a gum (ca. 2 g) which was purified by FCC eluting with System A (200:8:1) to give a gum (ca. 0.75 g) which was partitioned between 2 N hydrochloric acid (30 ml) and ethyl acetate (30 ml). The resultant precipitate, from which the liquid was carefully decanted, was partitioned between saturated potassium carbonate (30 ml) and ethyl acetate (3×30 ml). The combined organic extracts were evaporated to give a solid (ca. 260 mg) which was crystallised from absolute ethanol (15 ml) to give the free base of the title compound (0.15 g). This solid was dissolved in hot ethanol (30 ml) and treated with a solution of maleic acid (57 mg) in ethanol (2 ml) to precipitate on cooling the title compound (90 mg), m.p. 175°-176°.

Analysis Found: C,65.2; H,5.4; N,9.8;

$C_{19}H_{19}H_3O.C_4H_4O_4$ requires C,65.5; H,5.5; N,10.0%.

EXAMPLE 6

(E)-6,7,8,9-Tetrahydro-5-methyl-9-[(5-methyl-1H-imidazol-4-yl) methylene]cyclohept[b]indol-10(5H)-one Elution of the FCC column of Example 5 also gave a semi-solid (ca. 0.45 g) which was crystallised from absolute ethanol (25 ml) to give the title compound (0.3 g), m.p. 230°-232°.

Analysis Found: C,74.3; H,6.3; N,13.6;

$C_{19}H_{19}N_3O$ requires C,74.7; H,6.3; N, 13.8%.

EXAMPLE 7

1,2,3,9-Tetrahydro-9-methyl-3-[(1H-imidazol-4-yl)methylene]-4H-carbazol-4-one

A solution of diisopropylamine (1.54 ml) in dry THF (20 ml) at −78° was treated dropwise with n-butyllithium (1.32 M in hexane; 8.3 ml). The mixture was allowed to warm to 0° and was recooled to −78°. It was then added over 3 min, to a stirred suspension of 1,2,3,9-tetrahydro-9-methyl 4H-carbazol-4-one (2.0 g) in dry THF (80 ml) at −78°. The resultant suspension was then stirred at −78° for 2 h and was then treated with 1 -(triphenylmethyl)-1H-imidazole-4-carboxaldehyde (3.72 g). The mixture was stirred for a further 2 h, whilst it was slowly allowed to warm to room temperature and was then cooled to −78° and quenched with acetic acid (2 ml). The resultant solution was allowed to warm to room temperature and was poured into 8% aqueous sodium bicarbonate (600 ml).

The mixture was extracted with dichloromethane (3×150 ml) and the combined, dried organic extracts were evaporated to give a foam. A solution of this foam and p-toluenesulphonic acid monohydrate (18 g) in a mixture of acetic acid (25 ml) and dry THF (150 ml) was heated at reflux for 5 h. The cooled mixture was added cautiously to 8% aqueous sodium bicarbonate (650 ml) and was extracted with dichloromethane (3×150 ml). The combined, dried organic extracts were evaporated to to give a solid which was purified by FCC eluting with System A (100:10:1) to give the title compound (1.42 g), m.p. 225°-232°.

Analysis Found: C,73.3; H,5.6; N,14.7;

$C_{17}H_{15}N_3O$ requires C,73.6; H,5.5; N,15.1%.

EXAMPLE 8

1,2,3,9-Tetrahydro-9-methyl-3-[(5-methyl-1H-imidazol-4-yl)methylene]-4H-carbazol-4-one maleate A solution of 1,2,3,9-tetrahydro-9-methyl-3-[(5-methyl-1H-imidazol -4-yl)methylene]-4H-carbazol-4-one (3.50 g) in DMF (85 ml) and ethanol (50 ml) was added to a pre-reduced suspension of 10% palladium oxide on carbon (3.4 g) in ethanol (50 ml) and hydrogenated at room temperature and atmospheric pressure until uptake ceased (270 ml). The catalyst was filtered off and the filtrate evaporated. The residue was adsorbed from methanol (170 ml) onto SPCC silica and applied to an FCC column. Gradient elution with System A (967:30:3→912:80:8) afforded the free base of the title compound as a solide (2.32 g). A portion of this solid (500 mg) in hot ethanol (15 ml) was treated with a hot solution of maleic acid (224 mg) in ethanol (2 ml) and on cooling, the precipitate was collected to give the title compound (415 mg), m.p. 130.5°-137°, t.l.c. (System A 200:10:1) 0.30.

Analysis Found: C,63.2; H,5.5; N,9.7;

$C_{18}H_{19}N_3O.C_4H_4O_4$ 0.33$H_2O$ requires C,63.6; H,5.7; N,10.1%.

Water assay Found: 1.55% w/w $H_2O$≡0.33 mol.

$^1$H-N.m.r. ($d_6$-DMSO) δ1.8-1.98 (1 H,m) 2.1-2.25 (1 H,m), 2.25 (3 H,s), 2.68-2.84(2 H,m), 2.85-3.3(3 H,m), 3.75(3 H,s), 6.0(2 H,s-maleate), 7.18-7.32(2 H,m), 7.57(1 H, brd), 8.03(1 H, brd), 8.88(1 H,s).

EXAMPLE 9

1,2,3,9-Tetrahydro-3-[(5-methyl-1H-imidazol-4-yl)methyl]-4H-carbazol -4-one maleate A solution of 1,2,3,9-tetrahydro-3-[(5-methyl-1H-imidazol-4-yl)methylene]-4H-carbazol-4-one (5.2 g) in ethanol (100 ml) was hydrogenated at room temperature and atmospheric pressure over a stirred suspension of pre-reduced 10% palladium oxide on carbon catalyst (50% aqueous paste; 1.0 g) in ethanol (30 ml) for 4.5 h. The mixture was then filtered and evaporated to give an oil (ca. 5 g) which was purified by FCC eluting with System A (100:10:1) to give the free base of the title compound (3.96 g) as an oil. A sample (400 mg) was dissolved in ethanol (4 ml) and treated with a solution of maleic acid (170 mg) in ethanol (1.25 ml). The solvent was removed in vacuo and the residue was triturated with dry ether (5×25 ml) to give a solid (555 mg). This solid (ca. 500 mg) was dissolved in hot methanol (5 ml) and ethyl acetate (15 ml) was added. The solution was concentrated to a volume of 10 ml and allowed to cool. After 1 h the precipitated solid was collected to give the title compound (314 mg), m.p. 160°-162°.

Water Analysis Found: 0.36% w/w≡0.06 mol $H_2O$.

Analysis found: C,63.3; H,5.3; N,10.2;

$C_{17}H_{17}N_3O.C_4H_4O_4.0.06H_2O$ requires C,63.6; H,5.4; N,10.6%.

EXAMPLE 10

7-Fluoro1,2,3,9-tetrahydro-9-methyl-3-[(5-methyl-1H-imidazol-4-yl) -methyl]-4H-carbazol-4-one maleate A solution of 7-fluoro1,2,3,9-tetrahydro-9-methyl-3-[(5-methyl-1H-imidazol-4-yl)methylene]-4H-carbazol-4-one (315 mg) in ethanol (25 ml) was hydrogenerated at room temperature and atmospheric pressure over pre-reduced 10% palladium oxide on carbon (50% aqueous paste; 300 mg) for 2 h. The mixture was filtered and evaporated to give a foam which was purified by FCC eluting with System A (9.12:80:8) to give the free base of the title compound (230 mg) as a solid. This was dissolved in hot ethanol (30 ml) and treated with a solution of maleic acid (85 mg) in warm ethanol (3 ml). The resultant solution was evaporated and the residual oil was triturated with ether (40 ml) to give a powder (210 mg). This was combined with the mother liquors, evaporated, treated with 8% aqueous sodium bicarbonate (25 ml) and extracted were evaporated to give a solid which was dissolved in hot ethanol (20 ml) and diluted with a solution of maleic acid (86 mg) in ethanol (3 ml). The solution was evaporated and the residual solid crystallised from ethanol (5 ml) to give the title compound (202 mg), m.p. 153°-156°.

Analysis Found: C,61.6; H,5.2; N,9.6;

$C_{18}H_{18}FN_3O.C_4H_4O_4$ requires C,61.8; H,5.2; N,9.8%.

EXAMPLE 11

1,2,3,9-Tetrahydro-6-methoxy-9-methyl-3-[(5-methyl-1H-imidazol-4-yl) methyl]-4H-carbazol-4-one A solution of (E)-1,2,3,9-tetrahydro-6-methoxy-9-methyl-3-[(5-methyl-1H-imidazol-4-yl)methylene-4H-carbazol-4-one (200 mg) in absolute ethanol (15 ml) was hydrogenated at room temperature and atmospheric pressure over a stirred suspension of 10% palladium oxide on carbon catalyst (50% aqueous paste; 100 mg) in absolute ethanol (5 ml). The mixture was filtered and evaporated to give a foam (ca. 200 mg) which was purified by FCC eluting with System A (200:10:1) to give the title compound (154 mg) as a solide, m.p. 227°-229°, t.l.c. (System A 200:10:1) Rf 0.26.

EXAMPLE 12

6,7,8,9-Tetrahydro-5-methyl-9-[(5-methyl-1H-imidazol-4-yl)methyl]-cyclohept[b]indol-10(5H)-one maleate A solution of (E)- and (Z)-6,7,8,9-tetrahydro-5-methyl -9-[(5-methyl-1H-imidazol-4-yl)methylene]cyclohept[b]indol-10(5H)-one (0.4 g) in ethanol (250 ml) was hydrogenated at room temperature and atmospheric pressure over 10% palladium oxide on carbon (100 mg) for ca. 5 h. The catalyst was filtered off and washed with a further quantity of ethanol (100 ml). The filtrates were combined and evaporated to leave a gum (0.4 g) which was purified by FCC eluting with System A (200:8:1) to give an oil (0.32 g). This was dissolved in absolute ethanol (15 ml) and treated with a solution of maleic acid (120 mg) in ethanol (5 ml). The resulting solution was concentrated to ca. 5 ml and diluted with dry ether (5 ml) to precipitate the title compound (0.41 g), m.p. 160°-162°.

Analysis Found: C,64.9; H,6.0; N,9.8;

$C_{19}H_{21}N_3O.C_4H_4O_4$ requires C,65.2; H,6.0; N,9.9%.

EXAMPLE 13

1,2,3,9-Tetrahydro-9-methyl-3-[(1H-imidazol-4-yl)methyl]-4H-carbazol -4-one maleate A solution of 1,2,3,9-tetrahydro-9-methyl-3-[(1H-imidazol-4-yl) methylene]-4H-carbazol-4-one (1.37 g) in ethanol (100 ml) was hydrogenated at atmospheric pressure and room temperature over a 10% palladium on charcoal catalyst (50% aqueous paste; 130 mg). After ca. 30 min. a precipitate formed and THF (ca. 30 ml) was added to redissolve the precipitate. The mixture was stirred for a further 4 h and was then filtered. The filtrate was treated with maleic acid (569 mg) and the resultant solution was evaporated to give a solid which was recrystallised from a mixture of methanol and ethyl acetate to give the title compound (1.35 g), m.p. 175°-177°.

Analysis Found: C,64.2; H,5.5; N,10.6;

$Ch_{17}H_{17}N_3O.C_4H_4O_4$ requires C,63.8H,5.4; N,10.6%.

EXAMPLE 14

1,2,3,9-Tetrahydro-N,N,-dimethyl-3-[(5-methyl-1H-imidazol-4-yl)methyl]-4-oxo-9H-carbazol-9-carboxamide maleate A solution of Intermediate 7 (500 mg) in dry DMF (3 ml) was added dropwise to a stirred suspension of sodium hydride (52% dispersion in oil; 53 mg) in dry DMF (1 ml) under nitrogen. After 20 min. dimethylcarbamyl chloride (0.11 ml) was added and the mixture was stirred for 2 h. Water (50 ml) was added and the suspension was extracted with dichloromethane (3×25 ml). The combined, dried organic extracts were evaporated to give an oil (ca. 800 mg) which was dissolved in a mixture of THF (10 ml), acetic acid (10 ml) and water (10 ml) and heated at reflux for 1.5 h. The mixture was poured into saturated potassium carbonate solution (60 ml) and extracted with dichloromethane (3×30 ml). The combined, dried organic extracts were evaporated to give an oil (ca. 800 mg) which was purified by FCC eluting with System A (200:10:1) to give a foam (188 mg). This was dissolved in ethanol (3 ml) and treated with a solution of maleic acid (64 mg) in ethanol (0.5 ml). The solvent was removed in vacuo and the residue was triturated with dry ether (5×5 ml) to give the title compound (195 mg), m.p. 157°-158°.

Analysis Found: C,61.4; H,5.7; N,11.8;

$C_{20}H_{22}N_4O_2.C_4H_4O_4$ requires C,61.8; H,5.6; N,12.0%.

Examples 15 and 16 were prepared in a similiar manner to Example 14.

EXAMPLE 15

1,2,3,9-Tetrahydro-3-[(5-methyl-1H-imidazol-4-yl)methyl]-9-(phenylsulphonyl) -4H-carbazol-4-one maleate Intermediate 7 (500 mg) was reacted with benzene sulphonyl chloride (0.15 ml) to give the title compound (215 mg), m.p. 154°-156°.

Analysis Found: C,60.3; H,4.7; N,7.5;

$C_{23}H_{21}N_3O_3S.C_4H_4O_4$ requires C,60.6; H,4.7; N,7.9%.

EXAMPLE 16

Methyl 1,2,3,9-tetrahydro-3-[(5-methyl-1H-imidazol-4-yl)methyl]-4-oxo -9H-carbazol-9-acetate maleate Intermediate 7 (500 mg) was reacted with methyl chloroformate (0.09 ml) to give the title compound (155 mg), m.p. 167°-168°.

Analysis Found: C,60.8; H,5.0; N,9.1;

$C_{19}H_{19}N_3O_3.C_4H_4O_4$ requires C,60.9; H,5.1; N,9.3%.

EXAMPLE 17

1,2,3,9-Tetrahydro-3-[(5-methyl-1H-imidazol-4-yl)methyl]-9-(2-propenyl) -4H-carbazol-4-one maleate A solution of Intermediate 7 (500 mg) in dry DMF (10 ml) was added dropwise to a stirred suspension of sodium hydride (73% oil dispersion; (36 mg) in dry DMF under nitrogen and the resulting suspension was stirred at room temperature for 30 min, then a solution of allyl bromide (121 mg) in dry DMF (1 ml) was added and the resulting solution was stirred at room temperature for 1 h. The reaction mixture was then poured into water (500 ml) and extracted with dichloromethane (4×100 ml). The combined organic extracts were washed with water (3×250 ml), dried and concentrated to give an oil which was dissolved in a mixture of THF (5 ml), water (5 ml) and acetic acid (5 ml) and heated at reflux for 1.5 h. After cooling, the solution was basified with 2 N sodium carbonate solution and then extracted with dichloromethane (2×50 ml). The combined, dried organic extracts were concentrated to give an oil which was purified by FCC eluting with System A (150:8:1) to give the free base of the title compound (151 mg) as a solid. This was dissolved in dry methanol (20 ml), maleic acid (55 mg) was added and the resulting solution was heated on a steam bath for 10 min. The solution was then cooled, and ether (10 ml) was added to precipitate the title compound (174 mg), m.p. (194°-196°.

Analysis Found: C65.7; H,6.0; N,9.3;

$C_{20}H_{21}N_3O.C_4H_4O_4$ requires C,66.1; H,5.8; N,9.65%.

EXAMPLE 18

1,2,3,9-Tetrahydro-3-[(5-methyl-1H-imidazol-4-yl)methyl]-9-(cyclopentyl) -4H-carbazol-4-one maleate A solution of Intermediate 7 (750 mg) in dry DMF (30 ml) was added to a stirred suspension of sodium hydride (73% oil dispersion; 50 mg) in dry DMF (5 ml) under nitrogen and the resulting mixture was stirred at room temperature for 30 min. A solution of bromocyclopentance (223 g) in dry DMF (5 ml) was added and the resulting solution was stirred at room temperature under nitrogen for 8 h and then at 100°-110° for a further 18 h. After cooling the reaction mixture was poured into water (500 ml) and the resulting suspension was extracted with dichloromethane (3×100 ml). The combined organic extracts were washed with water (2×500 ml), dried and concentrated to give an oil which was adsorbed onto FCC silica. FCC eluting with System A (100:8:1) gave the free base of the title compound as an oil (77 mg). This was dissolved in dry methanol (10 ml), maleic acid (26 mg) was added and the resulting solution was heated on a steam bath for 10 min. The solution was cooled and ether (10 ml) was added to precipitate the title compound (82 mg), m.p. (194°-196°, t.l.c. (System A 100:8:1) Rf 0.35.

EXAMPLE 19

1,2,3,9-Tetrahydro-9-methyl-3-[(1-methyl-1H-imidazol-4-yl)methyl]-4H-carbazol-4-one maleate 1,2,3,9-Tetrahydro-9-methyl-3-[(1H-imidazol-4-yl)methyl]-4H -carbazol-4-one maleate (600 mg) was treated with 8% aqueous sodium bicarbonate (70 ml) and extracted with dichloromethane (3×25 ml). The combined, dried organic extracts were evaporated to give a foam (483 mg) which was dissolved in dry DMF (25 ml) at 5° and treated with sodium hydride (73% dispersion in oil; 59 mg). The mixture was stirred at 5° for 20 min. and was treated with methyl iodide (0.95 ml). The solution was stirred for a further 1 h and was treated with 8% aqueous sodium bicarbonate (10 ml). The suspension was diluted with water (120 ml) and extracted with dichloromethane (3×40 ml). The combined, dried organic extracts were evaporated to give a solide (641 mg) which was purified by FCC. Gradient elution with System A (100:3:0.3→100:10:1) gave a wax (432 mg) which was purified by high performance liquid chromatography (h.p.l.c.) (Spherisorb 5 sw column 25 cm×20 mm) eluting with chloroform:hexane:methanol:water 200:80:15:1 at 20 ml $min^{-1}$ giving, as the first eluted u.v. active component, an oil (110 mg). A solution of this oil and maleic acid (44 mg) in ethanol (15 ml) was evaporated to dryness to give the title compound (154 mg) as a solid, m.p. 138°-141°, t.l.c. (System A 100:10:1) Rf 0.4.

EXAMPLE 20

1,2,3,9-Tetrahydro-9-methyl-3-[(1-methyl-1H-imidazol-4-yl)methyl]-4H-carbazol-4-one maleate Further elution of the h.p.l.c. column of Example 19 gave a solid (50 mg). A solution of this solid and maleic acid (20 mg) in ethanol (10 ml) was evaporated to dryness to give the title compound (70 mg), m.p. 122°-125°, t.l.c. (System A 100:10;1) Rf 0.4.

EXAMPLE 21

1,2,3,9-Tetrahydro-6-hydroxy-9-methyl-3-[(5-methyl-1H-imidazol -4-yl)methyl]-4H-carbazol-4-one maleate Boron tribromide (1 M in dichloromethane; 1.4 ml) was added dropwise to a cold (0°) stirred solution of 1,2,3,9-tetrahydro-6-methoxy-9-methyl-3-[(5-methyl-1H-imidazol-4-yl)methyl-]-4H-carbazol-4-one (150 mg) in dry dichloromethane (15 ml) under nitrogen. After 1 h methanol (10 ml) was added and the solution was evaporated. The residue was purified by FCC eluting with System A (100:10:1) to give a solid (83 mg) which was dissolved in ethanol (ca. 20 ml) and treated with a solution of maleic acid (32 mg) in ethanol (ca. 2 ml). The solvent was removed in vacuo and the residue was triturated with dry ether (3×25 ml) to give the title compound (90 mg), m.p., 197°-199°, t.l.c. (System A 100:10:1) Rf 0.33.

EXAMPLE 22

3,4-Dihydro-4-methyl-2[(5-methyl-1H-imidazol-4-yl)methyl]cyclopent]b]indol-1(2H)-one maleate and hemimaleate A solution of lithium diisopropylamide (1.5 M in cyclohexane; 6 ml) was added dropwise to a cold (−70°) stirred suspension of 3,4-dihydro-4-methylcyclopent-[b]-1(2H)-one (1.5 g) in dry THF (90 ml) under nitrogen. The resulting solution was stirred at −70° for 15 min. and at 20° for 30 min. The solution was then recooled to −70° and treated with 4-(chloromethyl)-1-(triphenylemthyl)-1H-imidazole (3.0 g). The mixture was stirred at −70° for 2 h and then at 20° for 2 h and quenched with acetic acid (30 ml) and water (30 ml). The resulting mixture was left overnight and then heated on a steam bath in 1 h, cooled and partitioned between ethyl acetate (200 ml; discarded) and 2 N hydrochloric acid (2×100 ml). The acidic aqueous layer was basified (to pH 9) with potassium carbonate and extracted with a mixture of ethyl acetate:ethanol (20:1; 3×150 ml). The combined, dried organic extracts were evaporated to leave a foam (ca. 2 g) which was purified by FCC eluting with System A (150:8:1) to give a solid (0.72 g) which was triturated with absolute ethanol (5 ml). This solid (0.45 g) was dissolved in hot absolute ethanol (20 ml) and treated with a solution of maleic acid (187 mg) in ethanol (5 ml). The resulting solution was concentrated to ca. 5 ml and diluted with dry ether (10 ml) to precipitate a solid (0.6 g) which was recrystallised from a mixture of ethyl acetate:methanol (15:1; ca. 15 ml) to give the title compound hemimaleate; 0.2 g), m.p. 207°-208°.

Water Analysis Found 0.211% w/w≡0.04 mol $H_2O$.

Analysis Found: C,67.1; H,5.7; N,12.2;

$C_{17}H_{17}N_3O.0.5C_4H_4O.0.4H_2O$ requires C,67.5; H,5.7;N,12.4%.

A second crop of the title compound (full maleate salt; 0.3 g) was also obtained, m.p. 143°-145°, t.l.c. (System A 75:8:1) Rf 0.26.

EXAMPLE 23

6-Fluoro-1,2,3,9-tetrahydro-9-methyl-3-[(5-methyl-1H-imidazol-4-yl) methyl]-4H-carbazol-4-one maleate A solution of 3-methyoxy-6-[(5-methyl-1-(triphenylmethyl)-1H -imidazol-4-yl)methy]-2-cyclohexen-1-one (1.2 g) in a mixture of water (15 ml) and 2 N hydrochloric acid (2.7 ml) was stirred under nitrogen for 18 h. 1-Methyl-1-(4-fluorophenyl)hydrazine (378 mg) was added and the suspension was stirred at reflux under nitrogen for 2 h. The cooled mixture was poured into 8% aqueous sodium bicarbonate (60 ml) and extracted with ethyl acetate (2×50 ml). The combined, dried organic extracts were evaporated to give an oil (ca. 1.2 g) which was purified by SPCC eluting with System A (923:70:7) to give the free base of the title compound (240 mg) as a powder. This was dissolved in hot ethanol (15 ml), a solution of maleic acid (99 mg) in warm ethanol (2 ml) was added and the resultant solution was evaporated. The solid residue was crystallised from ethanol (6 ml) to give the title compound (175 mg), m.p. 148°-150°.

Water Analysis Found 2.17% w/w≡0.53 mol $H_2O$.

Analysis Found: C60.5; H,5.2; N,9.4;

$C_{18}H_{18}FN_3O.C_4H_4O_4O_4$. 0.53$H_2O$ requires C,60.5; H,5.3; N,9.6%.

EXAMPLE 24

1,2,3,9-Tetrahydro-6,9-dimethyl-3-[(5-methyl-1H-imidazol-4-yl)methyl]-4H-carbazol-4-one maleate In a similar manner to that described in Example 23, 3-methoxy-6 -[(5-methyl-1-(triphenylmethyl)-1H-imidazol-4-yl)methyl]-2-cyclohexen -1-one (1.14 g) was reacted with 1-methyl-1-(4-methylphenyl)hydrazine (350 mg). Purification by SPCC eluting with System A (934:60:6) gave the free base of the title compound (350 mg) as a solid. Maleate formation gave the title compound (205 mg), m.p. 150°-152°.

Analysis Found: C,64.8; H,5.8; N,9.7;

$C_{19}H_{21}N_2O.C_4H_4O_4$ requires C,65.2; H,6.0; N,9.9%.

EXAMPLE 25

1,2,3,9-Tetrahydro-3-[(5-methyl-1H-imidazol-4-yl)methyl]-9-(phenylmethyl) -4H-carbazol-4-one maleate A solution of 1,2,3,9-tetrahydro-3-[(5-methyl-1-(triphenylmethyl) -1H-imidazol-4-yl)methyl]-9-(phenylmethyl)-4H-carbazol-4-one (240 mg) in a mixture of acetic acid (7 ml), water (7 ml) and THF (7 ml) was heated at reflux for 2 h. The mixture was poured into saturated potassium carbonate solution (40 ml) and extracted with dichloromethane (3×20 ml). The combined, dried organic extracts were evaporated to give a solid (256 mg) which was purified by SPCC eluting with System A (200:10:1) to give a solid (99 mg). This was dissolved in ethanol (3 ml) and treated with a solution of maleic acid (33 mg) in ethanol (1 ml). The solvent was removed in vacuo and the residue was triturated with dry ether to give the title compound (128 mg), m.p. 142°-144°.

Water Analysis Found 0.27% w/w≡0.07 mol $H_2O$.

Analysis Found: C,68.7; H,5.6; N,8.5;

$C_{24}H_{23}N_3O.C_4H_4O_4$. 0.07$H_2O$ requires C,69.7; N,8.6%.

Examples 26 and 27 were prepared in a similar manner to Example 25 from the appropriate protected intermediate.

EXAMPLE 26

9-(Cyclopentylmethyl)-1,2,3,9-tetrahydro-3-[(5-methyl-1H-imidazol-4-yl) methyl]-4H-carbazol-4-one maleate The deprotection of 1,2,3,9-tetrahydro-9-(cyclopentylmethyl)-3-[5-methyl-1(triphenylmethyl)-1H-imidazol-4-yl)methyl]-4H-carbazol -4-one (255 mg) gave the free base of the title compound (127 mg). Maleate formation gave the title compound (144 mg), m.p. 178°-180°.

Water Analysis Found 0.37% w/w≡0.1 mol $H_2O$.

Analysis Found: C67.3; H,6.2; N,8.9;

$C_{23}H_{27}N_3O.C_4H_4O_4$. 0.1$H_2O$ requires C,67.7; H,6.6; N,8.8%.

EXAMPLE 27

1,2,3,9-Tetrahydro-3-[(5-methyl-1H-imidazol-4-yl)methyl]-9-(2-propynyl) -4H-carbazol-4-one maleate The deprotection of 1,2,3,9-tetrahydro-3-[(5-methyl-1-(triphenylmethyl) -1H-imidazol-4-yl)methyl]-9-(2-propynyl)-4H-carbazol-4-one (90 mg) and purification by FCC gave the free base of the title compound (30 mg). Maleate formation gave the title compound (40 mg), m.p. 189°-191°.

Water Analysis Found 1.4% w/w≡0.34 mol $H_2O$.

Analysis Found: C65.0; H,5.4; N,9.1;

$C_{20}H_{19}N_3O.C_4H_4O_4$. 0.34$H_2O$.0.125$C_2H_5OH$ requires C,65.4; H,5.5; N,9.4%.

EXAMPLE 28

(E)-1,2,3,9-Tetrahydro-9methyl-3-[(5-methyl-1H-imidazol-4-yl) methylene]-4H-carbazol-4-one methanesulphonate Lithium diisopropylamide (from n-butyllithium, 1.55 M in hexane; (57.3 ml) and diisopropylamide (11.64 ml) in THF (45 ml)) was added dropwise over 15 min. at −5° under nitrogen to a stirred suspension of 1,2,3,9-tetrahydro-9-methyl-4H-carbazol-4-one (15 g) in THF (510 ml). After 45 min., Intermediate 2 (26.5 g) was added in one portion and the resultant solution was stirred at −5° to +5° for 1.75 h. The solution was treated with acetic acid at below 20° and stirred for 1 h. Methanesulphonic acid (34 ml) was added and the mixture was stirred and heated under reflux for 16 h. The resultant suspension was cooled to 5°, stirred at below 5° for 1 h and the solid was filtered off. The product was washed with THF (2×50 ml) and dried in vacuo at 50° to give a solid (28.5 g) which was recrystallised from methanol to give the title compound (17 g), m.p. 264.5°-267°.

Analysis Found: C,54.5; H,5.3; N,9.75;

$C_{18}H_{17}N_30$.1.4$CH_4O_3S$ requires C,54.7; H,5.35; N,9.9%.

EXAMPLE 29

1,2,3,9-Tetrahydro-9-methyl-3-[(5-methyl-1H-imidazol-4-yl)methyl]-4H -carbazol-4-one A solution of (E)-1,2,3,9-tetrahydro-9-methyl-3-[(5-methyl-1H -imidazol-4-yl)methylene] methanesulphonate (10 g) in methanol (150 ml) and triethylamine (3.6 ml) was hydrogenated at room temperature and atmospheric pressure over a suspension of pre-reduced 10% palladium oxide on carbon catalyst (aqueous paste; 1 g)

in methanol (10 ml). The mixture was then filtered, concentrated to ca. 100 ml and heated to reflux. Water (50 ml) was added and the solution was cooled to 0°. The resultant solid was filtered off, washed with water (ca. 50 ml) and dried in vacuo at 50° to give the title compound (3.80 g). The $^1$H-n.m.r. and t.l.c. of this material were consistent with those obtained for the product of Example 8.

EXAMPLE 30

1,2,3,9-Tetrahydro-3-[(5-methyl-1H-imidazol-4-yl)methyl]-9-methyl-4H -carbazol-4-one hydrochloride monohydrate A suspension of 1,2,3,9-tetrahydro-3-[(5-methyl-1H-imidazol-4-yl) methyl]-9-methyl-4H-carbazol-4-one (20 g) in IMS (200 ml) was heated to boiling and 2 N hydrochloric acid (50 ml) was added. The resulting solution was allowed to cool to 20°, the resultant suspension was stirred for 1 h and then cooled at 4° for 2 h. The product was filtered off and dried in vacuo at 55° to yield the title compound (20.8 g), m.p. 290° (decomp.).

Analysis Found: C,62.1; H,6.25; N,12.05; Cl,9.85; $C_{18}H_{19}N_3O.HCl.H_2O$ requires C,62.5; H,6.4; N,12.15; Cl,10.25%.

EXAMPLE 31

(+)-1,2,3,9-Tetrahydro-9-methyl-3-[(5-methyl-1H-imidazol-4-yl)methyl]-4H-carbazol-4-one A solution of (±)-1,2,3,9-tetrahydro-9-methyl-3-[(5-methyl-1H -imidazol-4-yl)methyl]-4H-carbazol-4-one (500 mg) in warm methanol (30 ml) was treated with a solution of (+)-2,3,-bis-[[(4-methylphenyl) carbonyl-]oxy] butanedioic acid (690 mg) in methanol (10 ml) and the solution was allowed to stand at 0° for 3 days. It was then filtered to leave a solid which was recrystallised from methanl to give the desired salt (195 mg), m.p. 146°-148°. A portion of this salt (186 mg) was suspended in water (10 ml) and potassium carbonate solution (1 g in 15 ml water) was added and the mixture was extracted with dichloromethane (2×40 ml). The combined, dried organic extracts were evaporated in vacuo to leave the title compound (79.2 mg) as a solid, m.p. 230°-232°, $[\alpha]^{20}_D=-49.7°$ (c.=0.41%, $CHCl_3$).

EXAMPLE 32

(−)-1,2,3,9-Tetrahydro-9-methyl-3-[(5-methyl-1H-imidazol-4-yl)methyl]-4H-carbazol-4-one A solution of (±)-1,2,3,9-tetrahydro-9-methyl-3-[(5-methyl-1H -imidazol-4-yl)methyl]-4H-carbazol-4-one (500 mg) in warm methanol (30 ml) was treated with a solution of (−)-2,3,-bis-[[(4-methylphenyl) carbonyl-]oxy] butanedioic acid (690 mg) in methanol (10 ml) and the solution was allowed to stand at 0° for 3 days. It was then filtered to leave a solid which was recrystallised from methanl to give the desired salt (162 mg), m.p. 147°-149°. This was suspended in water (15 ml) and potassium carbonate solution (1 g in 10 ml water) was added, and the mixture was extracted with dichloromethane (2×30 ml). The combined, dried organic extracts were evaporated in vacuo to leave the title compound (72.5 mg) as a solid, m.p. 230°-232°, $[\alpha]^{20}_D-48.4°$ (c.=0.44%, $CHCl_3$).

EXAMPLE 33

1,2,3,9-Tetrahydro-9-methyl-3-[(5-methyl-1H-imidazol-4-yl)methyl]-4H -carbazol-4-one A solution of Intermediate 7 (190 mg) in dry DMF (1 ml) was added dropwise to a stirred suspension of sodium hydride (52% dispersion in oil; 20 mg) in dry DMF (0.4 ml) under nitrogen. After 15 min. iodomethane (0.027 ml) was added and the mixture was stirred for 1.5 h. Water (20 ml) was added and the suspension was extracted with dichloromethane (3×10 ml). The combined, dried organic extracts were evaporated to give an oil (ca. 300 mg) which was dissolved in a mixture of THF (4 ml), acetic acid (4 ml) and water (4 ml) and heated at reflux for 1.5 h. The mixture was poured into saturated potassium carbonate solution (20 ml) and extracted with dichloromethane (3×10 ml). The combined, dried organic extracts were evaporated to give a semi-solid (ca. 255 mg) which was purified by SPCC eluting with System A (200:10:1) to give the title compound (7 mg). The $^1$H-n.m.r. and t.l.c. of this material were consistent with those obtained for the product of Example 8.

EXAMPLE 34

1,2,3,9-Tetrahydro-9-methyl-3-[(5-methyl-1H-imidazol-4-yl)methyl]-4H -carbazol-4-one n-Butyllithium (1.45 M in hexane; 2.07 ml) was added dropwise to a cold (−70°) stirred solution of diisopropylamine (0.42 ml) in dry THF (20 ml) under nitrogen. The solution was allowed to reach 0° over 30 min, cooled to −70° and added to a cold (−70°) stirred solution of 1,2,3,9-tetrahydro-9-methyl-4H-carbazol-4-one (500 mg) in dry THF (10 ml) under nitrogen. Hexamethylphosphoramide (0.44 ml) was added and the mixture was allowed to reach 0° over 1 h. The solution was cooled to −70° and a suspension of 4-(chloromethyl)-5-methyl-1-(triphenylmethyl) -1H-imidazole (936 mg) in dry THF (15 ml) was added and the mixture was allowed to reach ca. 20° over 2.5 h. It was stirred for a further 18 h, poured into 8% sodium bicarbonate solution (100 ml) and extracted with dichloromethane (3×50 ml). The combined, dried organic extracts were evaporated to give a semi-solid which was treated with a mixture of acetic acid (10 ml), water (10 ml) and THF (10 ml) and heated at reflux for 1.5 h. The solution was poured into saturated potassium carbonate solution (100 ml) and extracted with dichloromethane (3×50 ml). The combined, dried organic extracts were evaporated to give a solid (ca. 1.8 g) which was purified by SPCC eluting with System A (200:10:1) to give the title compound (17 mg). The $^1$H-n.,m.r. and t.l.c. of this material were consistent with those obtained from the product of Example 8.

EXAMPLE 35

1,2,3,9-Tetrahydro-9-methyl-3-[(5-methyl-1H-imidazol-4-yl)methyl]-4H-carbazol-4-one 1,2,3,9-Tetrahydro-9-methyl-3-[(5-methyl-1H-imidazol-4-yl)methyl]-4H-carbazol maleate (37 mg) was partitioned between 2 N bicarbonate (10 ml) and chloroform (3×15 ml). The combined, dried organic layers were evaporated to give the free base (26 mg) which was dissolved in 10% aqueous THF (4 ml) at −10° under nitrogen. To this stirred solution, a solution of 2,3-dichloro-5,6-dicyano-1,4-benzoquinone (49 mg) in dry THF (1.6 ml) was added dropwise and the reaction mixture was allowed to warm to 0° over 3 h. The solution was evaporated in vacuo and purified by FCC eluting with System A (94.5:5:0.5) to give the title compound (10 mg) as a solid. The $^1$H-n.m.r. and t.l.c. of this material were consistent with those obtained for the product of Example 8.

EXAMPLE 36

1,2,3,9-Tetrahydro-3-[(5-methyl-1H-imidazol-4-yl)methyl]-9-methyl-4H -carbazol-4-one 3-Methoxy-6[(5-methyl-1-(triphenylmethyl)-1H-imidazol-4-yl) methyl]-2-cyclohexen-1-one (203 mg) was treated with a mixture of water (5 ml) and 2 N hydrochloric acid (0.45 ml) and the resultant solution was stirred at room temperature under nitrogen for 18 h. 1-Methyl-1-phenylhydrazine (0.05 ml) was added dropwise and stirring was continued for 7 h. Further 1-methyl-1-phenylhydrazine (0.05 ml) was added and stirring was continued at room temperature for 5 days. The suspension was poured into 8% aqueous sodium bicarbonate (10 ml) and extracted with ethyl acetate (3×15 ml). The combined, dried organic extracts were evaporated to give an oil (ca. 240 mg) which was purified by FCC eluting with System A (189:10:1) to give a solid (55 mg). A portion of this solid (40 mg) was heated at 85° with fused zinc chloride (450 mg) in glacial acetic acid (3 ml) for 5 h. The mixture was cooled, poured into 2 N aqueous sodium hydroxide (20 ml) and extracted with ethyl acetate (3×15 ml). The combined, dried organic extracts were evaporated to give an oil (ca. 20 mg) which was purified by FCC eluting with System A (89:10:1) to give the title compound (5 mg). The $^1$H-n.m.r. and t.l.c. of this material were consistent with those obtained for the product of Example 8.

EXAMPLE 37

1,2,3,9-Tetrahydro-9-methyl-3-[(5-methyl-1H-imidazol-4-yl)methyl]-4H-carbazol-4-one A solution of 1,2,3,9-tetrahydro-9-methyl-3-[[(5-methyl (triphenylmethyl)-1H-imidazol-4-yl)methyl]-carbazol-4-one (268 mg) in a mixture of glacial acetic acid (5 ml), THF (5 ml) and water (5 ml) was heated at 100°-110° for 8 h. After cooling, 2 N sodium hydroxide solution (50 ml) was added and the resulting suspension was extracted with dichloromethane (2×50 ml). The combined, dried organic extracts were concentrated to give a foam which was purified by FCC eluting with System A (100:8:1) to give the title compound (114 mg) as a solid. The $^1$H-n.m.r. and t.l.c. of this material were consistent with those obtained for the product of Example 8.

EXAMPLE 38

1,2,3,9-Tetrahydro-9-methyl-3-[(5-methyl-1H-imidazol-4-yl)methyl]-4H-carbazol-4-one A solution of N,N,5-trimethyl-4-[(2,3,4,9-tetrahydro-9-methyl-4-oxo -1H-carbazol-3-yl)methyl]-1H-imidazole-1-sulphonamide (400 mg) in 2 N hydrochloric acid (30 ml) and absolute ethanol (5 ml) was heated at 100°-110° for 8 h. Work up and FCC as described in Example 32 gave the title compound (261 mg) as a solid. The $^1$H-n.m.r. and t.l.c. of this material were consistent with those obtained for the product of Example 8.

EXAMPLE 39

1,2,3,9-Tetrahydro-3-[(5-methyl-1H-imidazol-4-yl)methyl]-9-methyl-4H -carbazol-4-one A solution of the products from Intermediate 16 (0.2 g) in 49% hydrobromic acid (3 ml) was stirred at 20° for 30 min. The mixture was then heated on a steam bath for 30 min. and refluxed gently (at ca. 150°) for 1.5 h. The mixture was diluted with water (20 ml) and washed with ethyl acetate (2×20 ml; discarded). The acidic aqueous phase was basified (to pH9) with potassium carbonate and extracted with ethyl acetate:ethanol (20:1; 2×30 ml). The combined, dried organic extracts were evaporated to leave a solid which was triturated with dry ether (5 ml) to give the title compound (0.09 g) as a solid. The $^1$H-n.m.r. and t.l.c. of this material were consistent with those obtained for the product of Example 8.

EXAMPLE 40

1,2,3,9-Tetrahydro-3-[(5-methyl-1H-imidazol-4-yl)methyl]-9-methyl-4H -carbazol-4-one A solution of the products from Intermediate 17 (0.5 g) in a mixture of absolute ethanol (20 ml) and 2 M hydrochloric acid (10 ml) was heated on a steam bath for 1 h. The resulting solution was concentrated in vacuo to ca. 20 ml, diluted with water (40 ml) and washed with ethyl acetate (2×40 ml; discarded). The acidic aqueous layer was basified (to pH 9) with potassium carbonate and extracted with ethyl acetate:ethanol (20:1; 2×50 ml). The combined, dried organic extracts were evaporated to give the title compound (0.34 g) as a solid. The $^1$H-n.m.r. and t.l.c. of this material were consistent with those obtained for the product of Example 8.

EXAMPLE 41

8-Fluoro-1,2,3,9-tetrahydro-3-[(5-methyl-1H-imidazol-4-yl)methyl]-4H -carbazol-4-one 8-Fluoro-1,2,3,9-tetrahydro-3-[(5-methyl-1H-imidazol-4-yl) methylene]-4H-carbazol-4-one (728 mg) in absolute ethanol (30 ml) was added to a suspension of 5% palladium on charcoal (100 mg) in ethanol (30 ml), and the resulting mixture was hydrogenated at room temperature and atmospheric pressure until hydrogen uptake had ceased. The mixture was filtered, and the filtrate was evaporated in vacuo to leave an oil which was purified by FCC eluting with ethanol:ethyl acetate (1:5) to give the title compound (342 mg), m.p. 135°-140°, t.l.c. (ethanol:ethyl acetate, 1:5) Rf 0.175.

EXAMPLE 42

8-Fluoro-1,2,3,9-tetrahydro-9-methyl-3-[(5-methyl-1H-imidazol-4-yl) methyl]-4H-carbazol-4-one 8-Fluoro-1,2,3,9-tetrahydro-9-methyl-3-[(5-methyl-1H-imidazol-4-yl) methylene]-4H-carbazol-4-one (1.5 g) was dissolved in ethanol (50 ml) and added to a suspension of 5% palladium on charcoal (200 mg) in ethanol (ca. 50 ml), and the resulting mixture was hydrogenerated at room temperature and atmospheric pressure until hydrogen uptake had ceased. The mixture was filtered, and the filtrate was evaporated in vacuo to give the title compound (1.5 g), m.p. 189°-191° (decomp.), t.l.c. (System A 100:8:1), Rf 0.43.

EXAMPLE 43

8-Fluoro-1,2,3,9-tetrahydro-3-[(5-methyl-1H-imidazol-4-yl)methyl]-4H -carbazol-4-one maleate 8-Fluoro-1,2,3,9-tetrahydro-3-[(5-methyl-1H-imidazol-4-yl)methyl]-4H -carbazol-4-one (330 mg) was dissolved in dry ethanol (20 ml). Maleic acid (129 mg) in ethanol (10 ml) was added, and the solution was evaporated in vacuo. The residue was triturated with ether and the resultant solid was crystallised from ethanol:ether to give the title compound (351 mg), m.p. 174°-177°.

Analysis Found: C,60.6; H,5.0; N,9.9;

$C_{21}H_{20}FN_3O_5$ requires C,61.0; H,4.9; N,10.2%.

EXAMPLE 44

8-Fluoro-1,2,3,9-tetrahydro-9-methyl-3-[(5-methyl-1H-imidazol-4-yl)methyl]-4H -carbazol-4-one maleate 8-Fluoro-1,2,3,9-tetrahydro-9-methyl-3-[(5-methyl-1H-imidazol-4-yl)methyl]-4H -carbazol-4-one (1.51 g) was dissolved in ethyl acetate (40 ml), and added to a solution of maleic acid (563 mg) in ethanol (50 ml). The solution was cooled to 0°, and the resultant solid was filtered off and dried in vacuo to give the title compound (1.61 g), m.p. 155°-158°, t.l.c. (System A 100:8:1), Rf 0.43.

The following examples illustrate pharmaceutical formulations according to the invention, containing 1,2,3,9-tetrahydro-9-methyl-3-[(5-methyl-1H-imidazol-1-yl)methyl]-4H-carbazol-4-one as the active ingredient. Physiologically acceptable salts and/or solvates of this compound, and other compounds of formula (I) and their physiologically acceptable salts and/or solvates may be formulated in a similar manner.

TABLETS FOR ORAL ADMINISTRATION

Tablets may be prepared by the normal methods such as direct compression or wet granulation.

The tablets may be film coated with suitable film forming materials, such as hydroxypropyl methylcellulose, using standard techniques. Alternatively the tablets may be sugar coated.

Direct Compression

| Tablet | mg/tablet |
|---|---|
| Active Ingredient | 0.50 |
| Calcium Hydrogen Phosphate BP* | 87.25 |
| Croscarmellose Sodium NF | 1.80 |
| Magnesium Stearate BP | 0.45 |
| Compression weight | 90.00 |

*of a grade suitable for direct compression.

The active ingredient was passed through a 60 mesh sieve, blended with the calcium hydrogen phosphate, croscarmellose sodium and magnesium stearate. The resultant mix was compressed into tablets using a Manesty F3 tablet machine fitted with 5.5 mm, flat bevelled edge punches.

| Sub-Lingual Tablet | mg/tablet |
|---|---|
| Active Ingredient | 0.5 |
| Compressible Sugar NF | 64.5 |
| Magnesium Stearate BP | 0.5 |
| Compression Weight | 65.0 |

The active ingredient is sieved through a suitable sieve, blended with the excipients and compressed using suitable punches. Tablets of other strengths may be prepared by altering either the ratio of active ingredient to excipients or the compression weight and using punches to suit.

Wet Granulation

| Conventional Tablet | mg/tablet |
|---|---|
| Active Ingredient | 0.5 |
| Lactose BP | 153.5 |
| Starch BP | 30.0 |
| Pregelatinized Maize Starch BP | 15.0 |
| Magnesium Stearate BP | 1.5 |
| Compression Weight | 200.0 |

The active ingredient is sieved through a suitable sieve and blended with lactose, starch and pregelatinised maize starch. Suitable volumes of purified water are added and the powders are granulated. After drying, the granules are screened and blended with the magnesium stearate. The granules are then compressed into tablets using 7 mm diameter punches.

Tablets of other strengths may be prepared by altering the ratio of active ingredient to lactose or the compression weight and using punches to suit.

| Sub-Lingual Tablet | mg/tablet |
|---|---|
| Active Ingredient | 0.5 |
| Mannitol BP | 58.5 |
| Hydroxypropylmethylcellulose | 5.0 |
| Magnesium Stearate BP | 1.0 |
| Compression Weight | 65.0 |

The active ingredient is sieved through a suitable sieve and blended with the mannitol and hydroxypropylmethylcellulose. Suitable volumes of purified water are added and the powders are granulated. After drying, the granules are screened and blended into tablets using suitable punches.

Tablets of other strengths may be prepared by altering the ratio of active ingredient to mannitol or the compression weight and punches to suit.

| CAPSULES | mg/tablet |
|---|---|
| Active Ingredient | 0.5 |
| *Starch 1500 | 98.5 |
| Magnesium Stearate BP | 1.0 |
| Fill Weight | 100.0 |

*a form of directly compressible starch.

The active ingredient is sieved and blended with a excipients. The mix is filled into size No. 2 hard gelatin capsules using suitable machinery. Other doses may be prepared by altering the fill weight and if necessary changing the capsule size to suit.

SYRUP

This may be either a sucrose free presentation.

| A. Sucrose Syrup | mg/5 ml dose |
|---|---|
| Active Ingredient | 0.5 |
| Sucrose BP | 2750.0 |
| Glycerine BP | 500.0 |
| Buffer | |

-continued

| A. Sucrose Syrup | mg/5 ml dose |
|---|---|
| Flavour | as required |
| Colour | |
| Preservative | |
| Purified Water BP to | 5.0 ml |

The active ingredient, buffer, flavour, colour and preservative are dissolved in some of the water and the glycerine is added. The remainder of the water is heated to dissolve the sucrose and is then cooled. The two solutions are combined, adjusted to volume and mixed. The syrup is clarified by filtration.

| B. Sucrose-Free | mg/5 ml dose |
|---|---|
| Active Ingredient | 0.5 |
| Hydroxypropylmethylcellulose USP (viscosity type 4000) | 22.5 |
| Buffer | as required |
| Flavour | |
| Colour | |
| Preservative | |
| Sweetener | |
| Purified Water BP to | 5.0 ml |

The hydroxypropylmethylcellulose is dispersed in hot water, cooled and then mixed with an aqueous solution containing the active ingredient and the other components of the formulation. The resultant solution is adjusted to volume and mixed. The syrup is clarified by filtration.

INJECTION FOR INTRAVENOUS ADMINISTRATION

| | mg/ml | |
|---|---|---|
| Active ingredient | 0.05 | 0.5 |
| Sodium Chloride BP | as required | as required |
| Water for Injection BP to | 1.0 ml | 1.0 ml |

Sodium chloride may be added to adjust the tonicity of the solution and the pH may be adjusted, using acid or alkali, to that of optimum stability and/or facilitate solution of the active ingredient. Alternatively, suitable buffer salts may be used.

The solution is prepared, clarified and filled into appropriate size ampoules sealed by fusion of the glass. The injection is sterilised by heating in an autoclave using one of the acceptable cycles. Alternatively, the solution may be sterilised by filtration and filled into sterile ampoules under aseptic conditions. The solution may be packed under an inert atmosphere of nitrogen or other suitable gas.

METERED DOSE PRESSURISED AEROSOL

| Suspension Aerosol | mg/metered dose | Per can |
|---|---|---|
| Active Ingredient micronised | 0.050 | 12.0 mg |
| Oleic Acid BP | 0.020 | 4.80 mg |
| Trichlorofluoromethane BP | 23.64 | 5.67 g |
| Dichlorodifluoromethane BP | 61.25 | 14.70 g |

The active ingredient is micronised in a fluid energy mill to a fine particle size range. The Oleic Acid is mixed with the Trichlorofluoromethane at a temperature of 10°-15° C. and the micronised drug is mixed into the solution with a high shear mixer. The suspension is metered into aluminium aerosol cans and suitable metering valves, delivering 85 mg of suspension are crimped onto the cans and the Dichlorodifluoromethane is pressure filled into the cans through the valves.

Solution Aerosol

| | mg/metered dose | Per can |
|---|---|---|
| Active Ingredient | 0.05 | 12.0 mg |
| Ethanol BP | 7.500 | 1.80 g |
| Trichlorofluoromethane BP | 18.875 | 4.53 g |
| Dichlorodifluoromethane BP | 48.525 | 11.65 g |

Oleic Acid BP, on a suitable surfactant e.g. Span 85 (sorbitan trioleate) may also be included).

The active ingredient is dissolved in the ethanol together with the Oleic Acid or surfactant if used. The alcoholic solution is metered into suitable aerosol containers followed by the trichlorofluoro-methane. Suitable metering valves are crimped onto the containers and dichlorodifluoromethane is pressure filled into them through the valves.

Inhalation Cartridges

| | mg/cartridge |
|---|---|
| Active Ingredient (micronised) | 0.05 |
| Laotose BP to | 25.00 |

The active ingredient is micronised in a fluid energy mill to a fine particle size range prior to blending with normal talbetting grade lactose in a high energy mixer. The powder blend is filled into No. 3 hard gelatin capsules on a suitable encapsulating machine. The contents of the cartridges are administered using a powder inhaler.

SUPPOSITORY

| | |
|---|---|
| Active Ingredient | 0.5 mg |
| *Witepsol H15 to | 1.0 g |

*Witepsol H15 is a proprietary grade of Adeps Solidus Ph. Eur.

A suspension of the active ingredient is prepared in the molten Witepsol and filled, using suitable machinery, into 1 g size supporitory moulds.

We claim:

1. A compound selected from:

8-fluoro-1,2,3,9-tetrahydro-9-methyl-3-[(5-methyl-1H-imidazol-4-yl)methyl]-4H-carbazol-4-one;

8-fluoro-1,2,3,9-tetrahydro-3-[(5-methyl-1H-imidazol-4-yl) methyl]-4H-carbazol-4-one;

and physiologically acceptable salts thereof.

2. A pharmaceutical composition for treating a condition caused by disturbance of "neuronal" 5 HT function which comprises an effective amount to relieve said condition of a compound as defined in claim 1 or a physiologically acceptable salt or solvate thereof together with at least one physiologically acceptable carrier or diluent.

3. A method of treating a condition caused by disturbance of "neuronal" 5 HT function which comprises administering to a patient an effective amount of a compound as defined in claim 1 or a physiologically acceptable salt or solvate thereof to relieve said condition.

4. A method according to claim 3 wherein said condition is anxiety.

5. A method according to claim 3 wherein said condition is a psychotic disorder.

* * * * *

UNITED STATES PATENT AND TRADEMARK OFFICE

CERTIFICATE OF CORRECTION

PATENT NO. : 5,202,343

DATED : April 13, 1993

INVENTOR(S) : Ian H. COATES et al.

It is certified that error appears in the above-identified patent and that said Letters Patent is hereby corrected as shown below:

On the Title Page, Item [75]:

Please delete the following inventors from the list of inventors:

James A. Bell
David C. Humber
George B. Ewan

Signed and Sealed this

Nineteenth Day of April, 1994

Attest:

BRUCE LEHMAN

*Attesting Officer* *Commissioner of Patents and Trademarks*